US010787696B2

(12) United States Patent
Oyler et al.

(10) Patent No.: US 10,787,696 B2
(45) Date of Patent: Sep. 29, 2020

(54) SYSTEM FOR THE ASSESSMENT OF PROTEASE ACTIVITY

(71) Applicant: IPSEN PHARMA S.A.S., Boulogne-Billancourt (FR)

(72) Inventors: George A. Oyler, Baltimore, MD (US); Yung-Nien Chang, Elkridge, MD (US); Yien Che Tsai, Frederick, MD (US)

(73) Assignee: IPSEN PHARMA S.A.S., Boulogne-Billancourt (FR)

( * ) Notice: Subject to any disclaimer, the term of this patent is extended or adjusted under 35 U.S.C. 154(b) by 0 days.

(21) Appl. No.: 14/026,014

(22) Filed: Sep. 13, 2013

(65) Prior Publication Data

US 2014/0017697 A1 Jan. 16, 2014

Related U.S. Application Data

(62) Division of application No. 12/962,610, filed on Dec. 7, 2010, now abandoned.

(60) Provisional application No. 61/267,386, filed on Dec. 7, 2009.

(51) Int. Cl.

| | |
|---|---|
| ***C12Q 1/37*** | (2006.01) |
| ***C12Q 1/6897*** | (2018.01) |
| ***C12N 15/63*** | (2006.01) |
| ***C12N 15/10*** | (2006.01) |

(52) U.S. Cl.

CPC .......... *C12Q 1/37* (2013.01); *C12N 15/1034* (2013.01); *C12N 15/1086* (2013.01); *C12N 15/635* (2013.01); *C12Q 1/6897* (2013.01)

(58) Field of Classification Search

CPC ...................................................... C12N 15/00

USPC .......................................................... 435/212

See application file for complete search history.

(56) References Cited

U.S. PATENT DOCUMENTS 6,699,702 B1 3/2004 Patel et al.
2005/0112682 A9* 5/2005 Kuhlemann ......... G01N 33/582 435/7.1

FOREIGN PATENT DOCUMENTS

WO WO2005076785 * 8/2005
WO WO2009048597 * 4/2009 ............... A23L 1/31

OTHER PUBLICATIONS

Nyborg et al, A signal peptide peptidase (SPP) reporter activity assay based on the cleavage of type II membrane protein substrates provides further evidence for an inverted orientation of the SPP active site relative to presenilin. J Biol Chem. Oct. 8, 2004;279(41):43148-56. Epub Jul. 12, 2004.*

Wang et al, Activation of ATF6 and an ATF6 DNA Binding Site by the Endoplasmic Reticulum Stress Response. J Biol Chem. Sep. 1, 2000;275(35):27013-20.*

Lebkowski et al, Adeno-associated virus: a vector system for efficient introduction and integration of DNA into a variety of mammalian cell types. Mol Cell Biol. Oct. 1988;8(10):3988-96.*

Fang et al, Evaluation of GAL4/TATA in Vivo. J Biol Chem. Feb. 27, 1998;273(9):4972-5.*

De la Luna et al, 1988. Efficient transformation of mammalian cells with constructs containing a puromycin-resistance marker. Gene 62:121-126.*

Mortensen et al, Selection of Transfected Mammalian Cells in: Current Protocols in Molecular Biology 9.5.1-9.5.13, Apr. 2009. John Wiley & Sons, Inc publisher.*

Filippova et al, An Exceptionally Conserved Transcriptional Repressor, CTCF, Employs Different Combinations of Zinc Fingers to Bind Diverged Promoter Sequences of Avian and Mammalian c-myc Oncogenes. Molecular and Cellular Biology, Jun. 1996, p. 2802-2813.*

Knoop et al, The Splicing Factor U1C Represses EWS/FLI-mediated Transactivation. J Biol Chem vol. 275, No. 32, Issue of Aug. 11, pp. 24865-24871, 2000.*

Geneswitch System, from Invitrogen Downloaded Aug. 14, 2019.*

Arnon, Stephen S., et al. Botulinum Toxin as a Biological Weapon Medical and public Health Management. JAMA. vol. 285, No. 8. pp. 1059-1070. 2001.

Bonetta, Laura. "The Inside Scoop—Evaluating Gene Delivery Methods." Nature Methods. vol. 2, No. 11. pp. 875-883. 2005.

Breidenbach, Mark A. et al. "New insights into clostridial neurotoxin—SNARE interactions." TRENDS in Molecular Medicine. vol. 11, No. 8. pp. 376-38. 2005.

Burnett, James C., et al. "Conformational sampling of the botulinum neurotoxin serotype a light chain: implications for inhibitor binding." Bioorganic & Medicinal Chemistry. vol. 13. pp. 333-341. 2005.

(Continued)

*Primary Examiner* — Sheridan Swope

(74) *Attorney, Agent, or Firm* — Gene J. Yao; Barnes & Thornburg LLP

(57) ABSTRACT

A system for the identification of proteases and protease inhibitors is provided. The system has at least two components. The first component is a reporter construct with at least one binding site, a transcriptional promoter, an inducible promoter region, and at least one reporter gene, all functionally connected for expression of the reporter gene(s) in functional coordination with a transcriptional activation agent. The second component is a transcriptional activation agent comprising a nucleic acid binding domain, at least one protease substrate domain, and at least one transcriptional activation domain for an inducible promoter. The system allows detection and evaluation of agents affecting protease activity directed to the protease substrate domain. The system also allows for the detection of the presence of proteases in environmental samples.

11 Claims, 14 Drawing Sheets

(56) References Cited

OTHER PUBLICATIONS

Burnett, James C., et al. "The Evolving Field of Biodefense: Therapeutic Developments and Diagnostics." Nature Reviews: Drug Discovery. vol. 4 pp. 281-297. 2005.
Montecucco, Cesar, et al. "Botulinal neurotoxins: revival of and old killer." Current Opinion in Pharmacology. vol. 5. pp. 274-279. 2005.
Chen, Sheng, et al. "Unique Substrate Recognition by Botulinum Neurotoxins Serotypes A and E." The Journal of Biological Chemistry. vol. 281, No. 16. pp. 10906-10911. 2006.
Chopra, Arun P., et al. "Anthrax Lethal Factor Proteolysis and Inactivation of MAPK Kinase." The Journal of Biological Chemistry. vol. 278, No. 11. pp. 9402-9406. 2003.
Comella, Cynthia L., et al. "Botulinum Toxins in Neurological Disease." Muscle & Nerve vol. 29. pp. 628-644. 2004.
Cornille, Fabrice, et al. "Cooperative Exosite-dependenent Cleavage of Sunaptobrevin by Tetanus Toxin Light Chain." The Journal of Biochemistry. vol. 272, No. 6. pp. 3459-3464. 1997.
Estojak, Joanne. "Correlation of Two-Hybrid Affinity Data with In Vitro Measurements." Molecular and Cellular Biology vol. 15, No. 10. pp. 5820-5829. 1995.
Foster, Keith A. "A new wrinkle on pain relief: re-engineering clostridial neurotoxins for analgesics." Drug Discovery Today. vol. 10, No. 8. pp. 563-569. 2005.
Hicks, Rickey P. "The Medicinal Chemistry of Botulinum, Ricin and Anthrax Toxins." Current Medicinal Chemistry. vol. 12. pp. 667-690. 2005.
Josko, Deborah. "Botulin Toxin: A Weapon in Terrorism." Clinical Laboratory Science. vol. 17, No. 1. pp. 30-34. 2004.
Kim, Sung Yun, et al. "In Vivo Determination of Substrate Specificity of Hepatitis C Virus NS3 Protease: Genetic Assay for Site-Specific Proteolysis: Analytical Biochemistry." vol. 284. pp. 42-48. 2000.
Kohorn, Bruce D. "Isolation of cDNAs Encoding Proteases of Known Specificity Using a Cleavable Gal4 Protein." Methods: A Companion to Methods in Enzymology. vol. 5. pp. 156-160. 1993.
Lacy, D. Borden, et al. "Crystal structure of botulinum neurotoxin type A and implications for toxicity." Nature Structural Biology. vol. 5, No. 10. pp. 898-902. 1998.
Lee, Hyun, et al. Local Structural Elements in the Mostly Unstructured Transcriptional Activation Domain of Human p53). The Journal of Biological Chemistry. Vo. 275, No. 38. pp. 29426-29432. 2000.
Lewis E. Diann, et al. Control of Adenovirus Late Promoter Expression in Two Human Cell Lines. Molecular and Cellular Biology. Vo. 5, No. 9. pp. 2433-2442. 1985.
Marks, James D. "Medical aspects of biologic toxins." Anesthesiology Clinics North America. vol. 22. pp. 509-532. 2004.
Meunier, Frederic A., et al. "Dynamics of motor nerve terminal remodeling unveiled using SNARE-cleaving botulinum toxins: the extent and duration are dictated by the sites of SNAP-25 truncation." Molecular and Cellular Neuroscience. vol. 22. pp. 454-466. 2003.
Nagai, Takeharu, et al. "A variant of yellow fluorescent protein with fast and efficient maturation for cell-biological applications." Nature Biotechnology. vol. 20. pp. 87-90. 2002.
Paddle, Brian M. "Therapy and Prophylaxis of Inhalded Biological Toxins." Journal of Applied Toxicology. vol. 23. pp. 139-170. 2003.
Park, Jong-Beak, et al. "Progress toward development of an inhalation vaccine against botulinum." Expert Review Vaccines. vol. 3, No. 4. pp. 477-487. 2004.
Ryan, Martin D., et al. "Foot-and-mouth disease virus 2A oligopeptide mediated cleavage of an artificial polyprotein." The EMBO Journal. vol. 13, No. 4. pp. 928-933. 1994.
Schiavo, Giampiertro, et al. "Botulinum G Neurotoxin Cleaves VAMP/Synaptobrevin at a Single Ala-Ala Peptide Bond." The Journal of Biological Chemistry. vol. 269, No. 32. pp. 20213-20216. 1994.
Schiavo, Giampiertro, et al. "Botulinum Neurotoxin Serotype F Is a Zinc Endopeptidase Specific for VAMP/Synaptobrevin." The Journal of Biological Chemistry. vol. 268, No. 16. pp. 11516-11519. 1993.
Schiavo, Giampiertro, et al. "Identification of the Nerve Terminal Targets of Botulinum Neurotoxin Serotypes A, D, and E." The Journal of Biological Chemistry. vol. 268, No. 32. pp. 23784-33787. 1993.
Schiavo, Giampiertro, et al. "Tetanus and botulinum-B neurotransmitter release by proteolytic cleavage of synaptobrevin." Nature. vol. 359. pp. 832-835. 1992.
Schmidt, James J., et al. "Botulinum Neurotoxin Serotype F: Identification of Substrate Recognition Requirements and Development of Inhibitors with Low Nanomolar Affinity." Biochemistry. Vo. 44. pp. 4067-4073. 2005.
Singh, Bal Ram. "Intimate details of the most poisonous poison." Nature Structural Biology. vol. 7, No. 8. pp. 617-919. 2000.
Swaminathan, Subramanyam, et al. "Structural analysis of the catalytic and binding cites of Clostridium botulinum neurotoxin B." Nature Structural Biology vol. 7, No. 8. pp. 693-699. 2000.
Turton, Kathryn, et al., "Botulinum and tetanus neurotoxins: structure, function and therapeutic utility." Trends Biochemistry Sciences. vol. 27, No. 11. pp. 552-558. 2002.
Van Poppel, Nicole F. J., et al. "Tight control of transcription in Toxoplasma gondii using an alternative test repressor." International Journal for Parasitology. vol. 36. pp. 443-452. 2006.
Verhaegen Monique, et al. "Bacterial Expression of in Vivo-Biotinylated Aequorin for Direct Application to Bioluminometric Hybridization Assays." Analytical Biochemistry. vol. 306. pp. 314-322. 2002.
Young, K.H. "Yeast Two-Hybrid: So May Interactions, (in) So Little Time." Biology of Reproduction. vol. 58. pp. 302-311. 1998.
International Search Report issued in corresponding PCT Application No. PCT/US2010/059341 dated Aug. 29, 2011.
Gunyuzlu, P. L., et al. "A yeast genetic assay for capspase cleavage of the am yloid-beta precursor protein." Molecular biotechnology. vol. 15(1). pp. 29-37 May 2000.

* cited by examiner

| Group | | 1 | 2 | 3 | Mean |
|---|---|---|---|---|---|
| RLU | +Tet | 536717 | 546409 | 645667 | |
| | -Tet | 2507 | 2551 | 3721 | |
| Fold of Activation | | 214.9 | 214.2 | 173.5 | 200.6 +/- 23.5 |

Evaluation of Stable BoNT/LC-B Indicator Cell Lines

- ■ Baseline
- □ 24-hr
- ▨ 48-hr

Y-axis: Fold Difference in RLU from GLuc Assay

X-axis: Indicator System
- Cleave-Off: BD | VAMP2 | AD
- Cleave-On: BD | AD | VAMP2

Functional Tests of Transactivator (TA) Constructs

| | BoNT/LC-A | | | | BoNT/LC-B | | | |
|---|---|---|---|---|---|---|---|---|
| TA Construct: | BD SNAP25 AD | | SNAP25 BD AD | | BD VAMP2 AD | | BD AD VAMP2 | |
| | Cleave-Off TA + | | Cleave-On TA + | | Cleave-Off TA + | | Cleave-On TA + | |
| Micrographs of Transient Transfection: | LC-A (+) | LC-A (-) | LC-A (+) | LC-A (-) | LC-B (+) | LC-B (-) | LC-B (+) | LC-B (-) |
| GLuc (RLU): | 41,477 | 814,944 | 361,402 | 838,670 | 27,064 | 620,283 | 630,156 | 6,761 |

SYSTEM FOR THE ASSESSMENT OF PROTEASE ACTIVITY

CROSS REFERENCE TO RELATED APPLICATIONS

This application is a divisional of U.S. patent application Ser. No. 12/962,610, entitled "METHOD FOR IDENTIFICATION OF PROTEASE ACTIVITY INHIBITORS AND ASSAYING THE PRESENCE OF PROTEASE ACTIVITY" and filed on Dec. 7, 2010, which claims the benefit of U.S. Provisional Application No. 61/267,386, entitled "BOTULINUM NEUROTOXIN INHIBITOR IDENTIFICATION METHOD AND SYSTEM" and filed Dec. 7, 2009, both of which are incorporated herein by reference in their entirety.

FIELD OF THE INVENTION

This invention generally relates to the field of protease inhibitor identification assays.

BACKGROUND

Proteases play an important role in biological processes. Proteases, however, can also cause significant harm to biological systems particularly those delivered by virus, toxins and pathogenic micro-organisms. Methods for developing protease inhibitors and assaying for protease activity particularly in cells is a critical area of biotechnology. For example, the Botulinum neurotoxins (BoNTs) are the most potent toxins known (S. S. Arnon, R. Schechter, et al. Jama 285:1059-70. (2001); and B. M. Paddle. J Appl Toxicol 23:139-70. (2003). Botulism can be caused by ingestion of food stuff contaminated with the bacteria Clostridium botulinum, colonization of open wounds by the bacterium, or ingestion or respiration of the toxin(s). These toxins represent a serious threat to both military personnel and civilian populations (S. C. Clarke. Br J Biomed Sci 62:40-6 (2005); R. P. Hicks, M. G. Hartell, et al. Curr Med Chem 12:667-90 (2005); D. Josko. Clin Lab Sci 17:30-4 (2004). The lethal dose in humans is <1 ng/kg of body weight. J. C. Burnett, E. A. Henchal, et al. Nat Rev Drug Discov 4:281-97 (2005); J. C. Burnett, J. J. Schmidt, et al. Bioorg Med Chem 13:333-41 (2005); B. M. Paddle J Appl Toxicol 23:139-70 (2003). The Centers for Disease Control and Prevention has listed these toxins as category A (the highest priority) bio-threat agents. Although BoNTs can be dangerous, they have been recognized as useful medicinal compounds. BoNTs are now established biotherapeutics for a range of physical ailments and cosmetic treatments and are being produced in increasing quantities, both domestically and overseas. R. Bhidayasiri, and D. D. Truong, J Neurol. Sci. 235:1-9 (2005); C. L. Comellaand and S. L. Pullman. Muscle Nerve 29:628-44 (2004); K. A. Foster. Drug Discov Today 10:563-9 (2005); R. G. Glogau. Clin J Pain 18:S191-7 (2002); J. D. Marks. Anesthesiol Clin North America 22:509-32, vii. (2004); C. Montecucco and J. Molgo. Curr Opin Pharmacol 5:274-9 (2005). A negative consequence of their usefulness is the increased availability of the neurotoxins for misuse. Likewise, increased usage increases the likelihood of the occurrence of unintended adverse effects during treatment. T. R. Cote, A. K. Mohan, et al. J Am Acad Dermatol 53:407-15 (2005).

Once inhaled into the lung or ingested into the gastrointestinal tract, the BoNTs are transcytosed across the respiratory epithelium or mucosa into the blood stream, where they can enter the intercellular space prior to binding to and entering the peripheral cholinergic presynaptic nerve endings. Currently, critical care mechanical ventilation is the only treatment option once neurons have been affected and diaphragm muscles cease to function. However, the effects of internalized BoNTs can last for months. R. Eleopra, V. Tugnoli, et al. Neurosci Lett 256:135-8 (1998); F. A. Meunier, G. Lisk, et al. Mol Cell Neurosci 22:454-66 (2003). As such, long-term mechanical ventilation would be impractical if even a limited number of individuals were simultaneously affected.

There are seven BoNT serotypes (A-G), which possess different tertiary structures and significant sequence divergence. Structurally, each serotype is composed of a 100 KDa heavy chain (HC) and a 50 KDa light chain (LC). They are synthesized initially as a single polypeptide chain, which is severed by bacterial or host proteases. The chains remain connected by a disulfide bridge until reaching the reducing cytosolic environment of the neuronal target cells. D. B. Lacy, W. Tepp, et al. Nat Struct Biol 5:898-902 (1998). L. L. Simpson. Annu Rev Pharmacol Toxicol 44:167-93 (2004). The LC is a zinc-dependent endopeptidase.

Once inhaled into the lung or ingested into the digestive tract, BoNTs are transcytosed across the mucosal epithelium into the blood stream, where they can enter the intracellular space prior to accessing peripheral cholinergic presynaptic nerve endings. The HC serves as a delivery system for the proteolytic LC by binding to neurons and transporting the LC into the cytosol via the carboxyl terminal half of the HC ($HC_C$) and transporting the LC into the cytosol from the endosomes via a pore formed by the aminal terminal half of the HC ($HC_N$). The LC of each BoNT serotype is a protease that cleaves a component of the SNARE proteins, which are responsible for acetylcholine containing vesicle fusion and release at the neuromuscular junctions. B. R. Singh. Nat Struct Biol 7:617-9 (2000); and K. J. Turton, A. Chaddock, and K. R. Acharya, Trends Biochem. Sci. 27:552-8 (2002). BoNT serotypes A and E cleave SNAP-25 (synaptosomal-associated protein (25 kDa). T. Binz, J. Blasi, et al. J Biol Chem 269:1617-20 (1994). Serotypes B, D, F and G cleave VAMP (vesicle-associated membrane protein, also referred to as synaptobrevin and VAMP-2). G. Schiavo, F. Benfenati, et al. Nature 359:832-5 (1992); G. Schiavo, C. Malizio, et al. J. Biol. Chem. 269:20213-6 (1994); G. Schiavo, O. Rossetto, et al. J Biol Chem 268:23784-7 (1993); G. Schiavo, C. C. Shone, et al. J Biol Chem 268:11516-9 (1993); J. J. Schmidt, and R. G. Stafford. Biochemistry 44:4067-73 (2005). Serotype C cleaves both SNAP-25 and syntaxin1a. J. Blasi, E. R. Chapman, et al. Embo J 12:4821-8 (1993). BoNT mediated cleavage of the SNARE proteins results in flaccid paralysis, by preventing motor neurons from releasing acetylcholine at the neuromuscular junctions and interrupting the function of autonomic nerves via the inhibition of acetylcholine release as well. Once diaphragm muscles are affected, breathing is impaired and ultimately suffocation results.

The seven BoNT serotypes differ significantly in amino acid sequence. However, the different serotypes adopt similar overall protein folds and aspects of the catalytic core are conserved. M. A. Breidenbachand A. T. Brunger. Trends Mol Med 11:377-81 (2005). The X-ray crystal structures of BoNT/A and BoNT/B indicate that the areas within 8 Å of the zinc-binding site of these two serotypes are highly homologous with 17 of the 22 residues being identical. S. Swaminathan & S. Eswaramoorthy, Nature Structural Biology 7:693-699 (2000). However, significant variation is observed within 15 Å, including at the zinc-binding pocket, which is buried much more deeply in BoNT/A than in BoNT/B. Therefore, the active sites differ sufficiently among the serotypes, such that broad-spectrum potential inhibitors are unlikely. Furthermore, upon binding, the substrate wraps around the circumference of BoNT L C, creating an unusually large substrate enzyme interface. M. A. Breidenbachand A. T. Brunger. Nature 432:925-9 (2004). BoNT substrate specificity is also determined by its binding of the substrate over the long substrate/LC protease interface through sites distal to the active site, which is called "exosite" binding. M. A. Breidenbachand A. T. Brunger. Trends Mol Med 11:377-81 (2005).

Vaccine approaches will likely play a role in biodefense against BoNT. M. P. Byrne and L. A. Smith. Biochimie 82:955-66 (2000). J. B. Park and L. L. Simpson. Expert Rev Vaccines 3:477-87 (2004). However, identification and inoculation of all members of large at risk populations prior to exposure is problematic. The development of therapeutic approaches that are effective post-exposure treatment is essential. Low molecular weight, non-peptidic inhibitors offer the best opportunity for the development of post-exposure therapeutics. Interruption of later steps in the pathway, and particularly proteolytic steps, is desirable for post-exposure therapy. Such compounds would have to be capable of penetrating into the cytoplasm of the intoxicated neurons and would need to act with specificity.

BRIEF DESCRIPTION OF THE DRAWINGS

The numerous advantages of the present invention may be better understood by those skilled in the art by reference to the accompanying drawings in which.

The transcriptional promoter region comprises at least two elements: at least one binding site ("BS") sequence that functionally corresponds to the BD domain of the TA agent and a Minimal Promoter ("MP") region having at least one TATA box sequence. The system illustrated in this figure is called the "cleave off" system because when the protease of the PC cleaves the PS, transcription stops and signal decreases.

FIGS. 2A and 2B are schematic representations of the three constructs generally described in FIGS. 1A and 1B, for illustration/exemplary purposes the domains illustrated as part of the TA agent are: the BD derived from transcriptional factor for the Gal4 operon, the PS is either VAMP2 (amino acids 25-94) or SNAP25 (amino acids 104-206), and the AD is the nuclear factor KB ("NFκB/AD"). The elements illustrated as part of the RC in FIG. 1B are: a promoter consisting of at least one BS corresponding to the Gal4 BD of the TA agent and a minimal adenovirus promoter region comprising the TATA box (E. D. Lewis, J. L. Manley, Mol. Cell Biol. 5: 2433-2442 (1985). The PC comprises the CMV promoter with a TetO sequence for regulation of expression and the SBP-CFP-BoNT/LC-A sequence for expression of BoNT/A light chain. Other constructs may include the light chains of any botulinum toxin or a protease that cleaves the PS on the TA agent.

FIGS. 3A and 3B are a schematic representation of a system in accordance with one embodiment of the present invention in which the BD and AD of the TA agent are attached to the end of the PS. Where the PS is localized to a membrane or kept outside the nucleus of the cell. When the protease is added to the system, it cleaves the PS releasing the BD-AD pair and enhancing transcription of the Reporter Gene ("RG"). This system is referred to as the "cleave on" system.

Figure 4A:
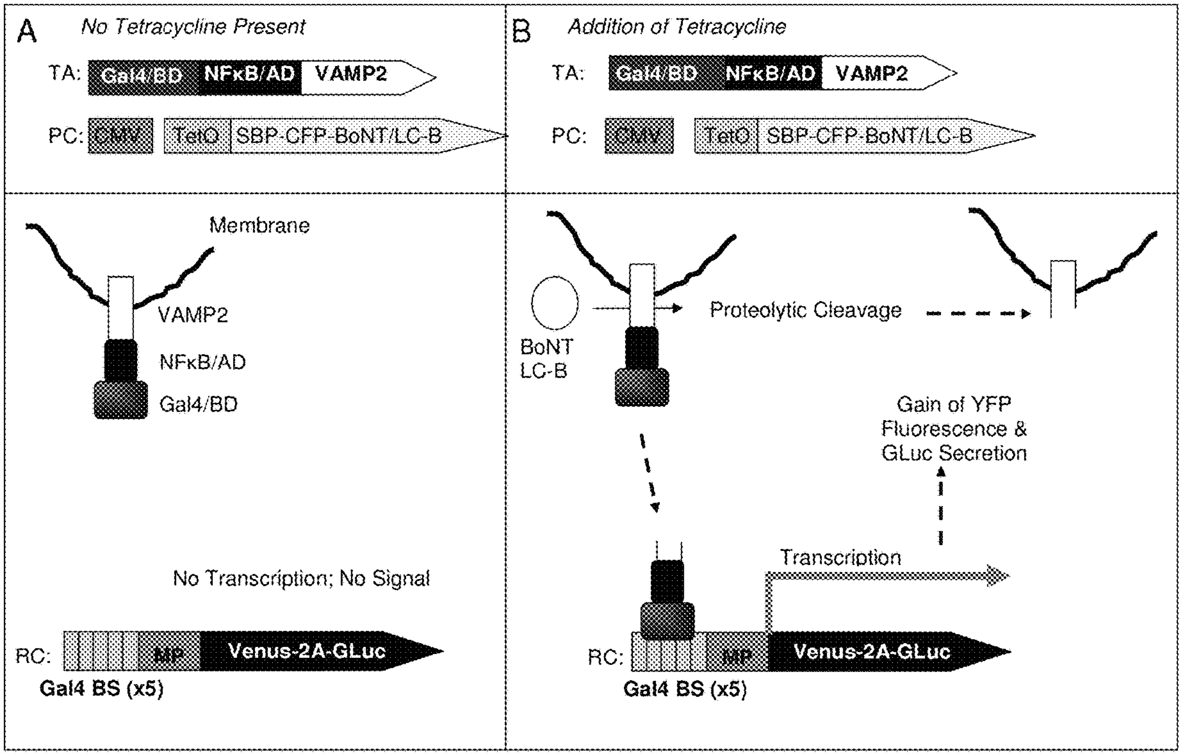
Figure 4B:
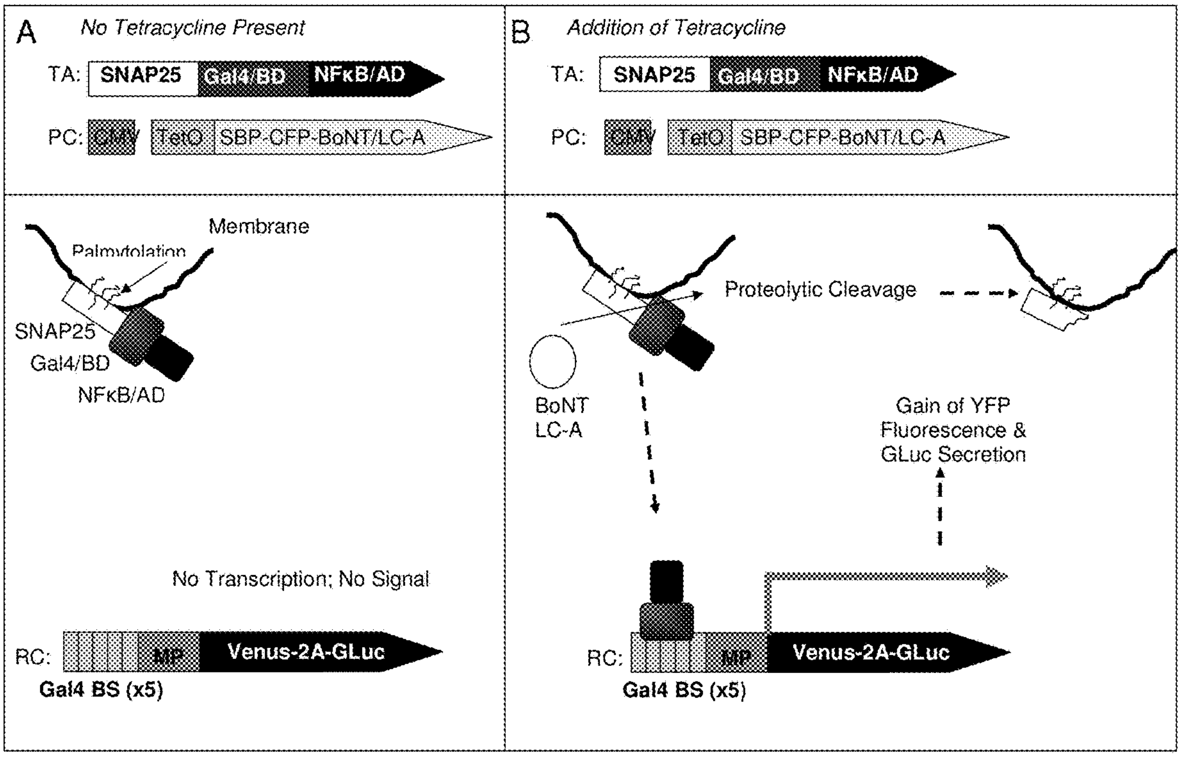

FIG. 4*a* is a schematic representation of the "cleave on" system where the PS is VAMP-2 and FIG. 4*b* is a schematic representation of the "cleave on" where the PS is SNAP-25.

Figure 5:
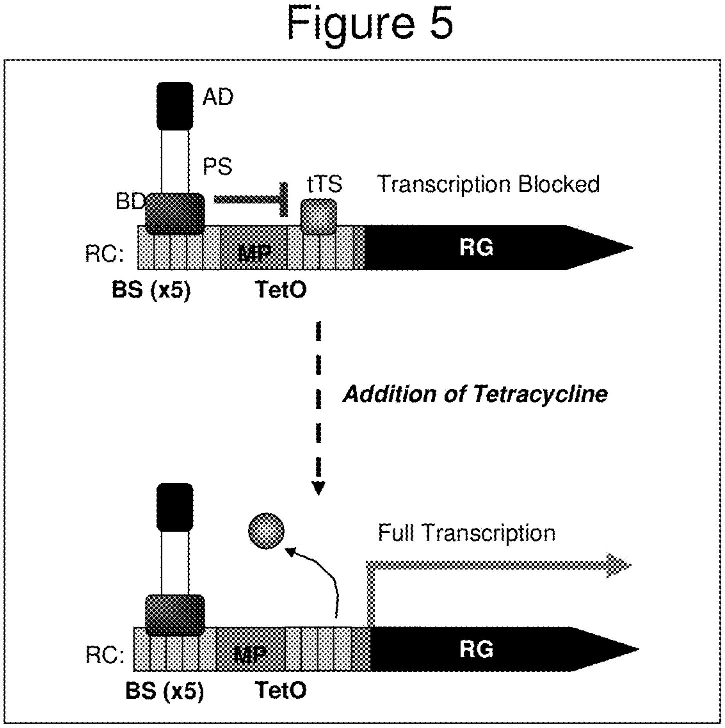

FIG. 5 is a schematic representation of a TA agent and a RC, which have an additional element to control any leakage of the minimal promoter. The additional element is at least one copy of a transcription regulator, in one preferred embodiment the transcription regulator is the TetO promoter region (5'-tccctatcagtgatagagatc-3'). Specifically, in the illustrated embodiment, the construct employs four copies of the TetO promoter sequence.

Figure 6:
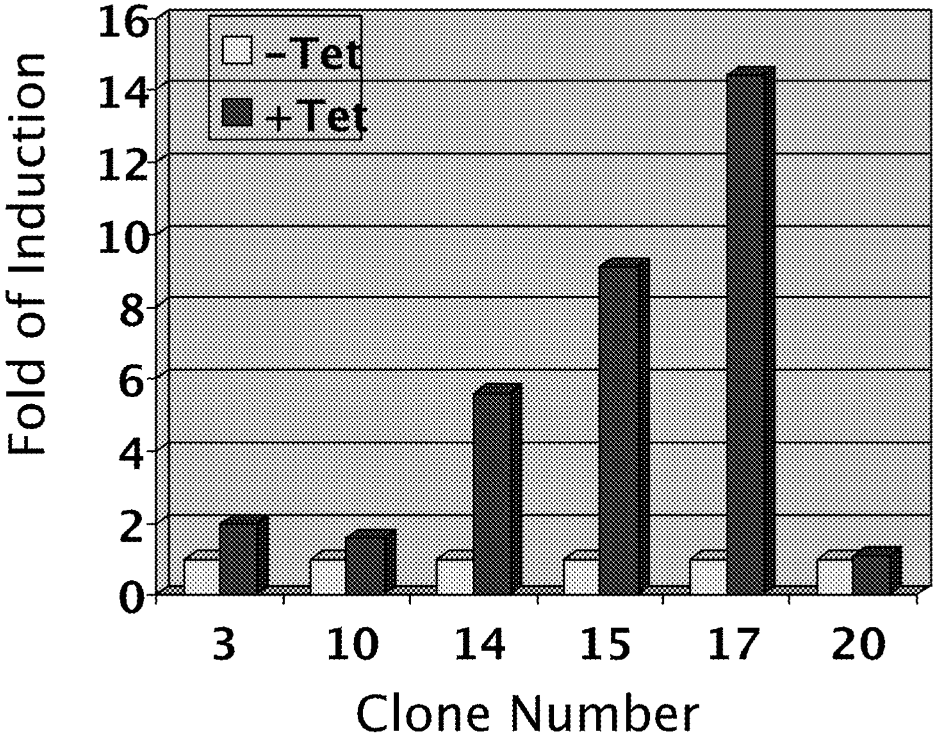

FIG. 6 a bar graph of the results of experiments showing the ratio of bioluminescence in the presence and absence of tetracycline for stably integrated RCs. The clones in this figure do not contain the TA agent construct.

Figure 7:
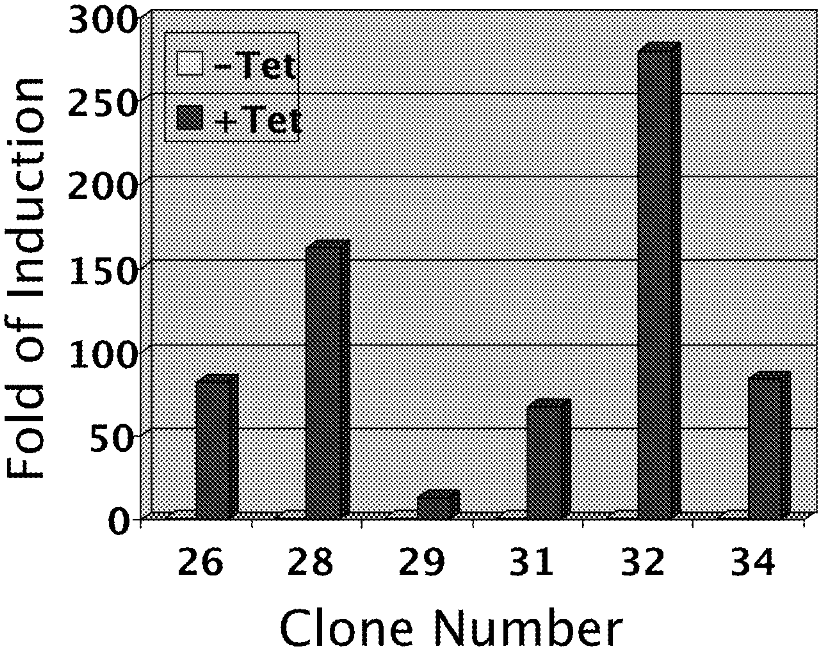

FIG. 7 is a bar graph of the results of experiments showing the ratio of bioluminescence in the presence and absence of tetracycline for stable reporter in the presence of TA agent.

Figure 8:
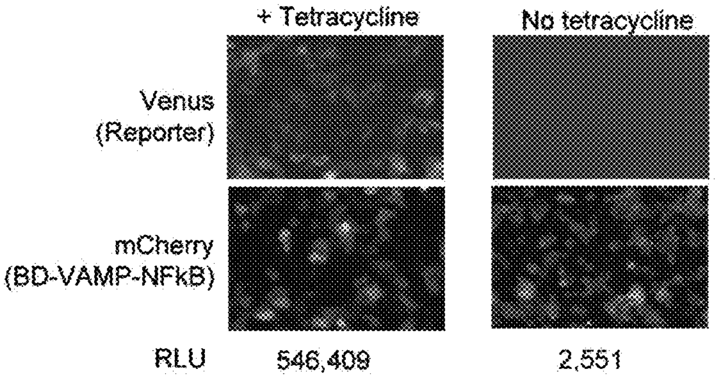

FIG. 8 shows the results of a microplate cell-based assay of cells containing a reporter construct and the indicated BD-VAMP-NFκB TA agent in the presence and absence of tetracycline.

Figure 9:
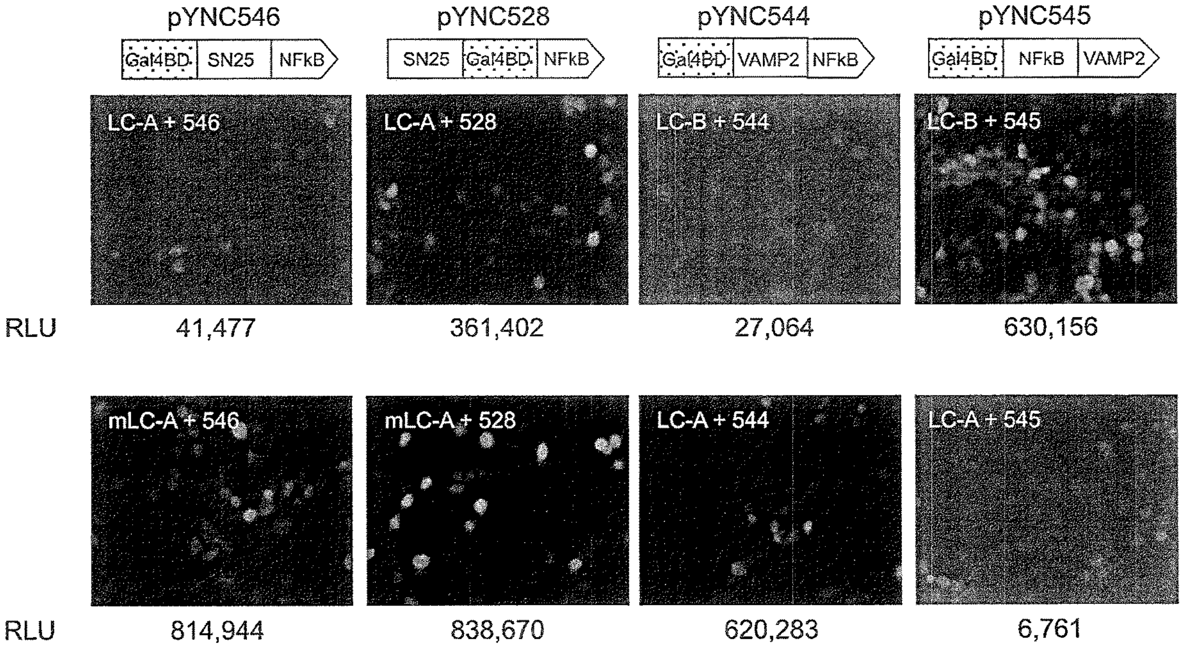

FIG. 9 is a bioluminescence assay in accordance with one preferred embodiment of the present invention showing the effect of the indicated TA agents on YFP (Venus) and GLuc expression.

Figure 10:
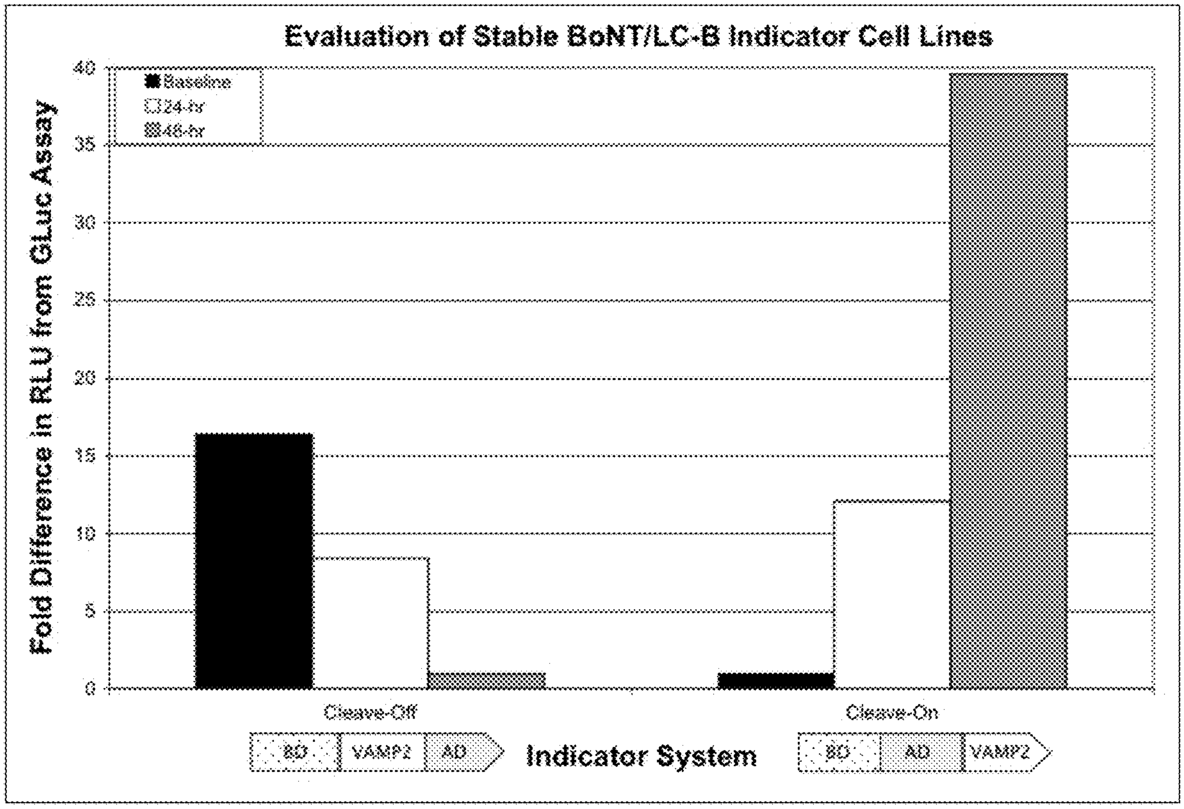

FIG. 10 is a bar graph of the results of experiments showing the evaluation of stable BoNT/LC-B indicator cell lines.

Figure 11:
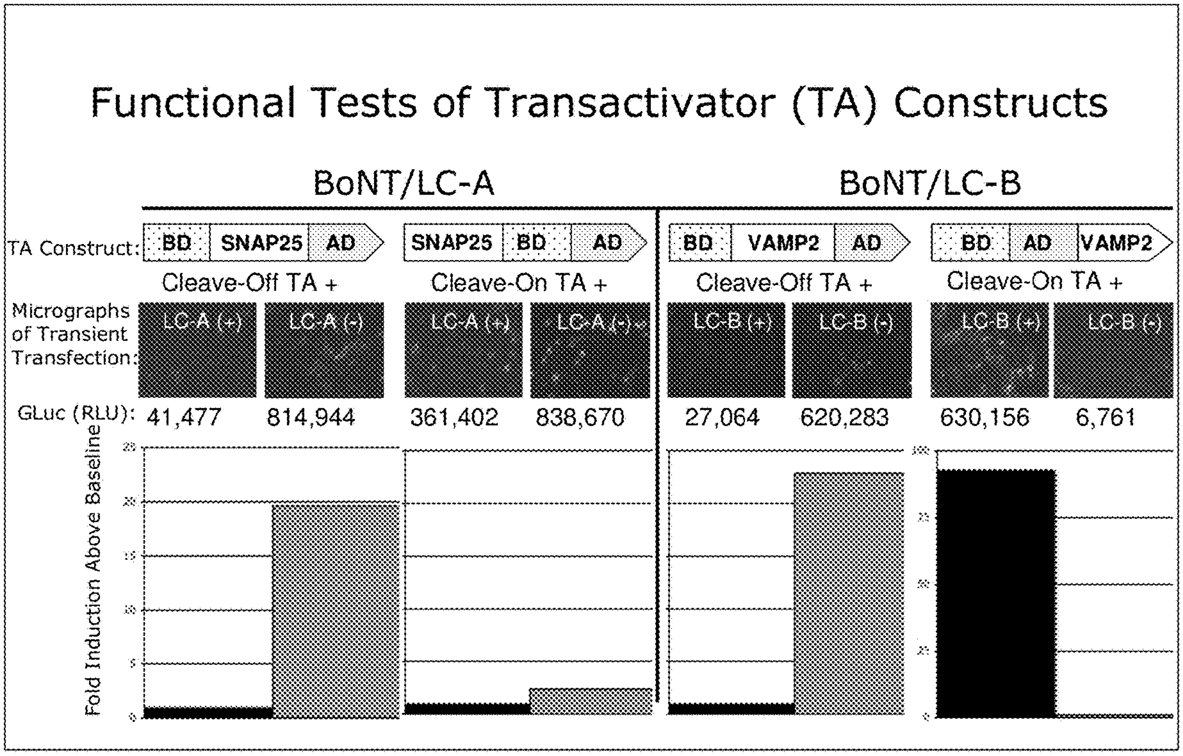

FIG. 11 is a bar graph and pictures of bioluminescence results of a functional test of the TA agent constructs.

Figure 12:
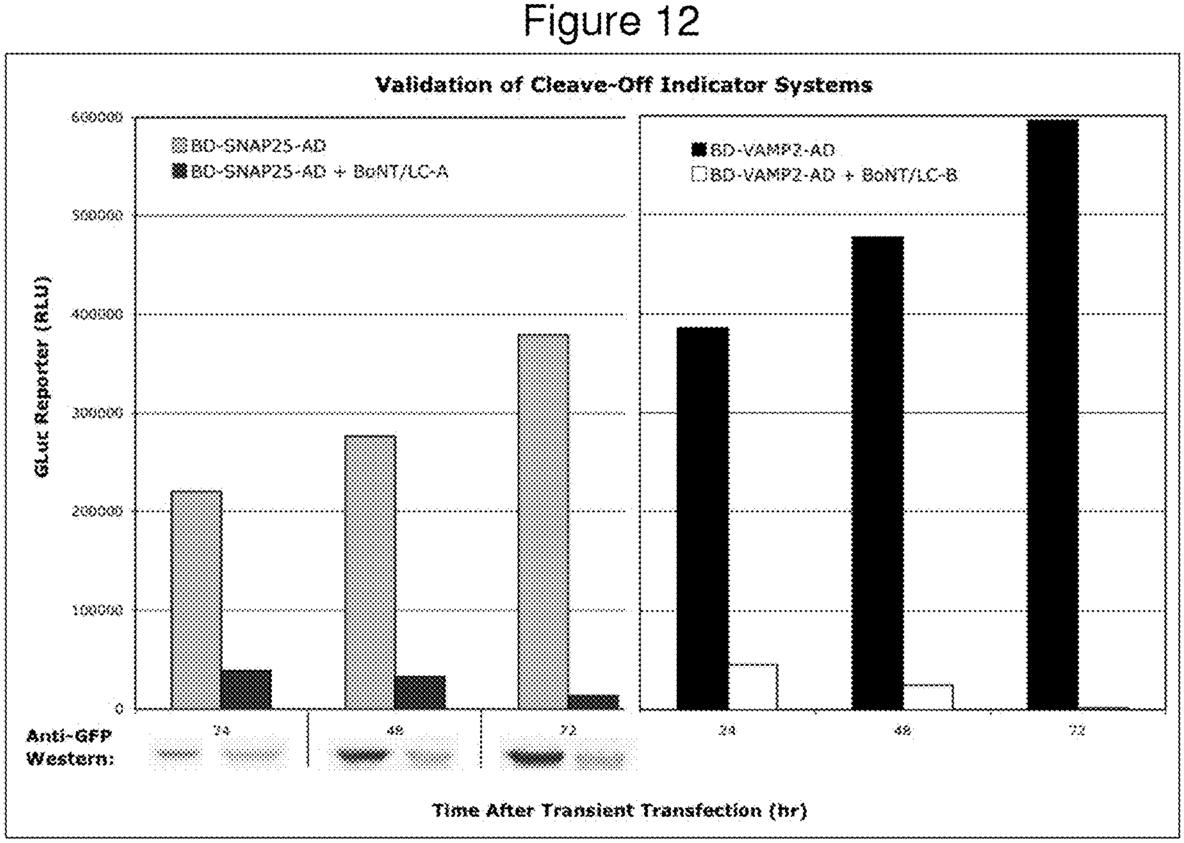

FIG. 12 is a bar graph showing validation of the cleave off indicator system.

Figure 13:
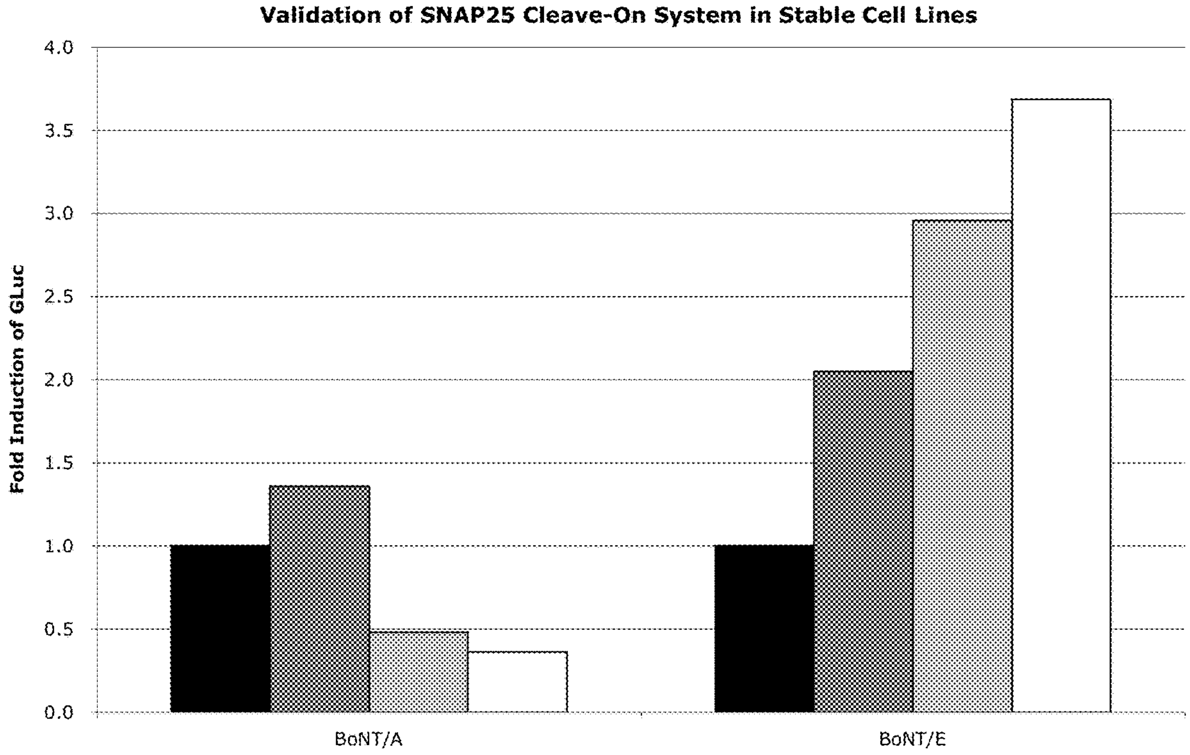

FIG. 13 is a bar graph showing validation of the cleave on system in stable cell lines.

SUMMARY OF THE INVENTION

A system for the identification of proteases and protease inhibitors is provided. The system has at least two components. The first component is a reporter construct with at least one binding site, a transcriptional promoter, an inducible promoter region, and at least one reporter gene, all functionally connected for expression of the reporter gene(s) in functional coordination with a transcriptional activation agent. The second component is a transcriptional activation agent comprising a nucleic acid binding domain, at least one protease substrate domain, and at least one transcriptional activation domain for an inducible promoter. The system allows detection and evaluation of agents affecting protease activity directed to the protease substrate domain. The system may also include at least one protease or protease candidate that specifically cleaves the protease substrate domain of the transcriptional activation agent.

A second preferred embodiment of the present invention is a method to identify protease inhibitors utilizing the system described above. Yet another embodiment of the present invention provides for a method to identify the presence of proteases in an environmental sample utilizing the system described above.

DETAILED DESCRIPTION

The invention summarized above may be better understood by referring to the following description, which should be read in conjunction with the accompanying claims and drawings. The description of embodiments, set out below to enable a person of ordinary skill in the art to make and use the invention, is not intended to limit the invention, but to serve as particular examples thereof. Those skilled in the art would appreciate that they may readily use the concept and specific embodiments disclosed as a basis for modifying or designing alternative, elements, methods and systems for carrying out the present invention.

Figure 1:
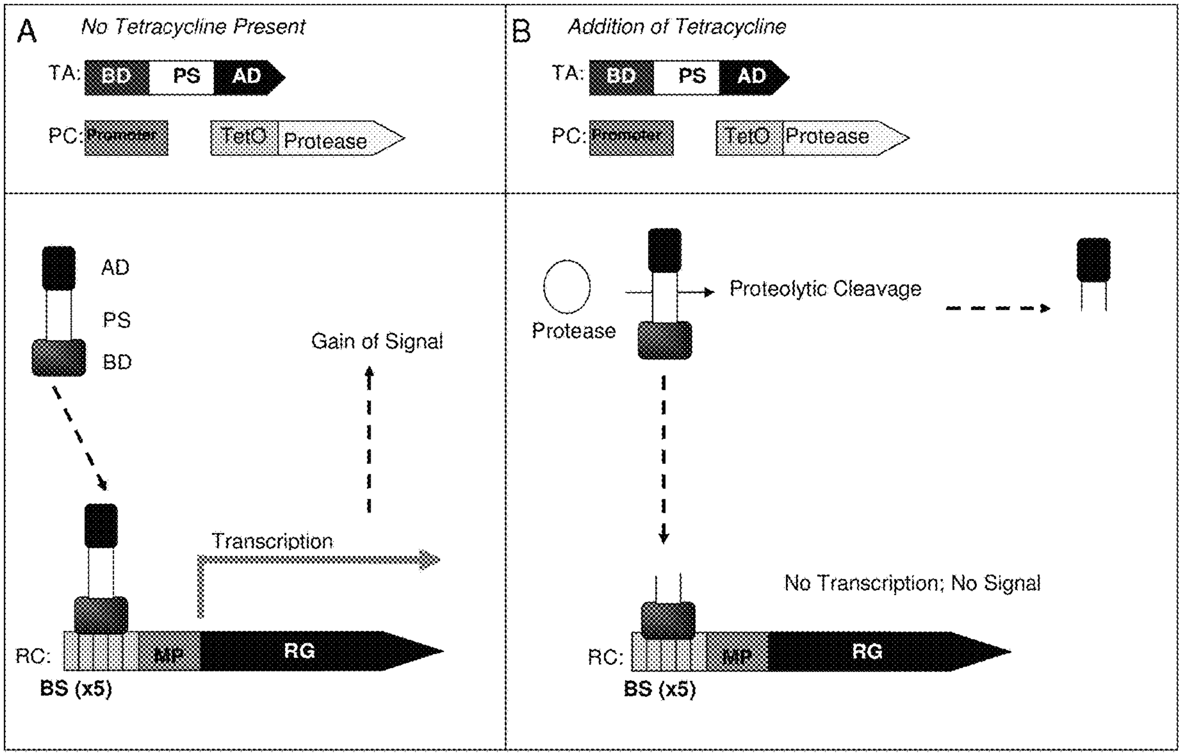
FIGS. 1A and 1B are schematic diagrams of three constructs made in accordance with one embodiment of the invention and their interaction with other molecules for assessing the change in the transcription signal of a reporter in the presence of a protease. One construct provides a Transcriptional Activator agent ("TA"). The TA agent comprises a Binding Domain ("BD"), a Protease Substrate ("PS") domain, and a transcriptional Activation Domain ("AD"). The second construct is a Protease Construct ("PC"). The PC comprises a promoter, a regulator sequence, e.g. TetO, and the sequence of a protease, which proteolytic activity cleaves the PC of the TA. The third construct is a Reporter Construct ("RC"). The RC of one preferred embodiment comprises a transcriptional promoter region and the Reporter Gene(s) ("RG").
Figure 2:
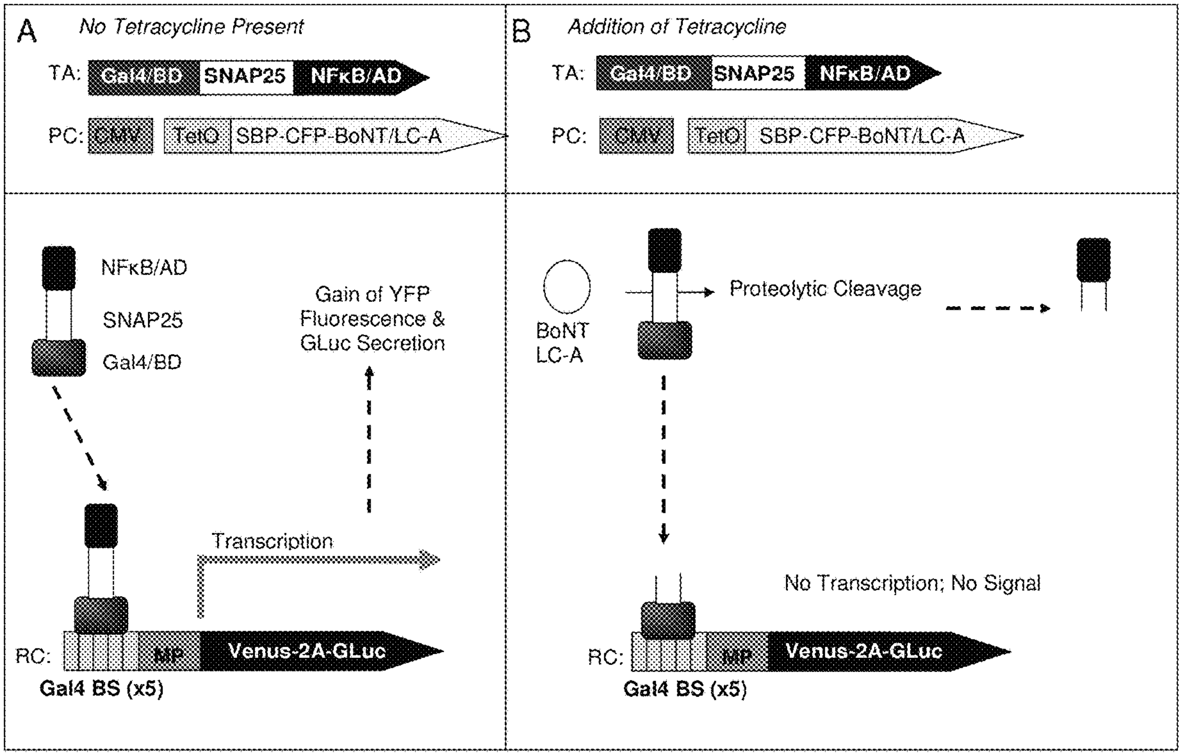
Figure 3:
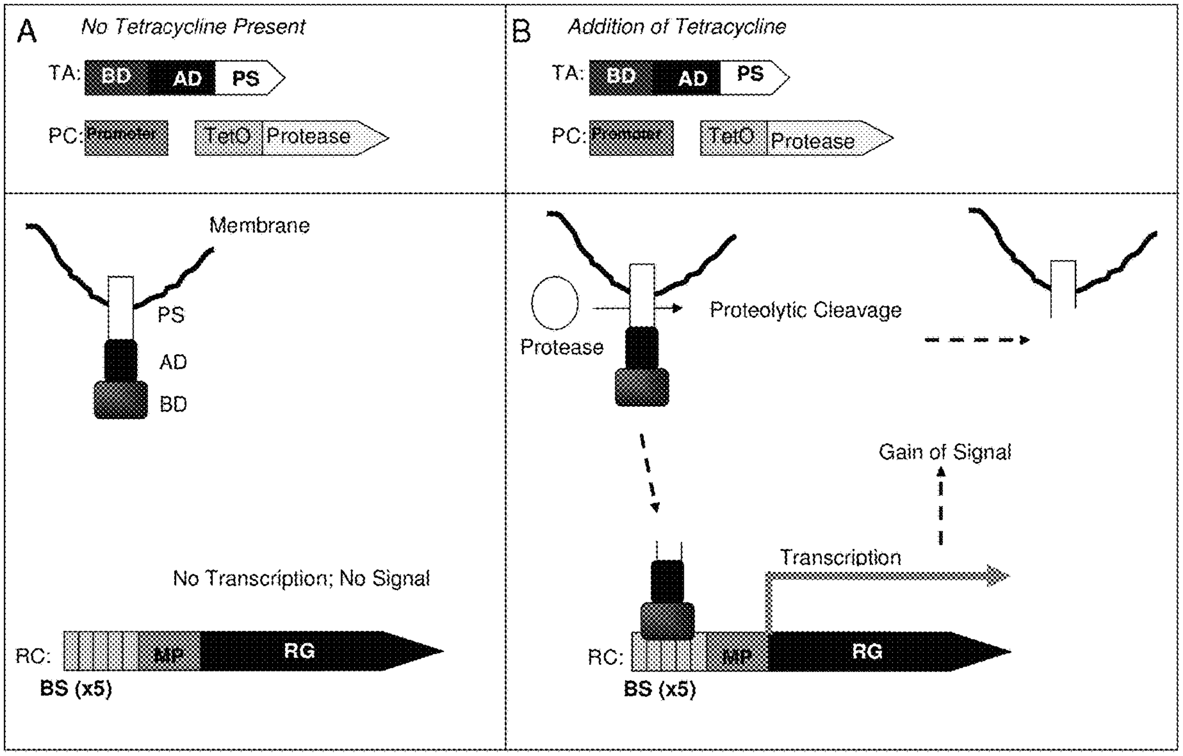

One embodiment of the present invention provides a novel, cell-based system for identification of protease inhibitors and evaluation of protease activity. The components of the system comprise multiple constructs. As shown FIGS. 1 through 5, three constructs form part of the system: a Transcriptional Activation agent ("TA", sometimes herein also referred to as "transactivator" construct), a Reporter Construct ("RC"), and a Protease Construct ("PC"). The three constructs can be utilized in two types of protease evaluation systems. In a "cleave off" system as shown in FIGS. 1 and 2, the product of the PC inactivates the TA, resulting in a decrease in transcription of the product of the RC. In a "cleave on" system as shown in FIGS. 3 and 4, the product of the PC releases the active portion of the TA agent activating transcription and enhancing signal from the reporter of the RC.

The TA agent is engineered to express a chimeric protein molecule comprising three elements: a DNA Binding Domain ("BD"), a Protease Substrate domain ("PS") comprising the cleavage site for at least one protease, and a transcription Activation Domain ("AD"). In one preferred embodiment of the present invention, the TA agent is designed so that the BD and the transcriptional activation domain AD are on opposite sides of the PS as described in FIGS. 1 and 2. In other embodiments of the present invention, the PS is on one end of the BD-AD elements of the TA agent as shown in FIGS. 3 and 4. Whether the system is a "cleave on" or "cleave of" system depends upon the position of the PS in the TA agent.

The TA agent according to one preferred embodiment utilizes botulinum toxin substrates, such as SNAP-25 or VAMP-2. The selected domains of SNAP-25 and VAMP-2 in these constructs are sufficient to allow cleavage activity. Accordingly, domains sufficient to encompass the protease substrate domain of either protein in respect to the BoNT proteases that normally cleave the respective substrate are provided. More preferably, the PS domain provided is sufficiently large to at least encompass also the exotoxin PS sites. M. A. Breidenbach and A.T.B. TRENDS in Molecular Medicine 11: 376-381(2005). For VAMP-2, the PS domain would comprise amino acids 25-94 of VAMP-2. Cornille F, Martin L, et al. J Biol Chem. 272:3459-64 (1997); Sikorra S, Henke T, et al. J Biol Chem. 283:21145-52 (2008). For SNAP-25, that domain would comprise amino acids 104-206 of SNAP-25. S. Chen and J. T. Barbieri, Journal of Biological Chemistry 281: 10906-10911 (2006). In one preferred embodiment, the sequence of the AD constructs are BD-SNAP-25-NFκB or BD-VAMP-NFκB. The SNAP-25 and VAMP-2 fragments utilized lack their palmitoylated residues, thus preventing localization of the TA agent to the plasma membrane or cellular vesicles respectively.

The PC includes a protease that recognizes a Protease Substrate ("PS") in the TA agent. The PC may be a vector expressing the protease and capable of being expressed in the host cell containing the TA and RC as shown in FIGS. 1 through 5. In one embodiment of the present invention, the protease is expressed in a vector as described in Example 3 below. In an alternative embodiment, the PC can be a protease or a protease like molecule introduced into the cell expressing the TA and RC. The protease of the PC cleaves the PS domain of the TA agent. In accordance with one embodiment, the AD of the TA agent is brought into proximity of the promoter on the RC by the BD, promoting transcription of a reporter located transcriptionally downstream from the BS of the RC as shown on FIGS. 1 and 2. When the PC is activated, or present in the host system, the proteolytic activity of the protease acts to deactivate and render ineffective the TA agent as a transcriptional enhancer by separating the BD from the AD, as shown in FIGS. 1B and 2B. In a preferred embodiment, the protease is selected from among BoNT A, C and E, and the PS is SNAP-25. In an alternative preferred embodiment, the protease is selected from among BoNT B, D, F and G, and the PS is VAMP-2. In a yet another preferred embodiment, the BoNT is serotype C and the PS is syntaxin1a (GenBank: AAK54507.2). In one embodiment, the TA may include a domain of syntaxin1a that lacks its c-terminal transmembrane domain (BD-syntaxin1a (1 to 265)-AD). The protease substrate may be any known protease substrate. It is expected that various proteases may also be utilized. Examples include the anthrax protease, caspases, alpha virus NSP2 protease, HIV processing proteases, Sumo processing proteases, Ubiquitin processing proteases, ISG15 processing protease, autophagy related ATG4 like processing proteases, and Hepatitis C processing proteases.

In accordance to other embodiments, cleavage of the PS domain results in enhanced expression of the reporter gene (the "cleave on" effect) as shown in FIGS. 3B and 4B. If the cleavage releases a unit comprising both the BD and AD elements functionally connected, transcription is enhanced. As shown in FIGS. 3B and 4B, the TA agent consisting of a BD and an AD can be kept outside the nucleus by palmitoylated residues on the protease substrate (PS) domain. In yet further embodiments, the BD-AD pair may be attached to other molecules that keep the BD-AD construct outside the nucleus of the cell until the protease from the PC releases the BD-AD construct, which is transported into the nucleus and then enhances transcription of the reporter gene. In such arrangement the protease substrate domain may be attached to the plasma membrane or other vesicular membranes in the cell. The cleavage site of the protease is located between the TA consisting of the BD-AD and the extra-nuclear anchoring site of the PS. Thus, when the PS is cleaved by the protease, the BD-AD is freed to enter the nucleus and enhance transcription of the indicator, signaling the presence of the protease. In one embodiment of the present invention, expression of the protease in the PC is regulated. For example, a TetO control element may be included upstream of the protease gene preventing expression of the protease unless the appropriate conditions are present. In one preferred embodiment, the TetO operator is utilized, which prevents expression of the protease in the absence of Tetracycline. It is contemplated that other control mechanisms known to individuals of ordinary skill in the art would also be appropriate for controlling the expression of the protease in the host cells.

The RC is a nucleic acid based construct. Preferably, the TA agent and/or the PC are also nucleic acid based constructs that express the trans-activator molecule and the protease, respectively. However, a person having ordinary skill in the art would recognize that the TA and/or the PCs may be provided as pre-made proteins to a functional mammalian cell. Likewise, an artisan skilled in the art can understand the application of the three construct system in other backgrounds, e.g. a cell-free system, where either or both the TA agent and the PC are provided as nucleic acid or proteins, where of the three constructs may be fixed on membranes and so on. In the description, below, the focus is on the preferred embodiment, where each of the constructs is a transgenic genetic construct introduced into a mammalian cell, preferably a human cell.

The RC has one or more BS recognized by the BD of the TA agent, a promoter sequence preferably comprising a TATA box and at least one reporter gene as shown in FIGS. 1 through 4. The BD element of the TA agent binds to the one or more BS elements. In one embodiment of the present invention the Gal4 BD is used in the TA agent and the corresponding Gal4 BS is used in the RC. In another preferred embodiment the LexA BD and corresponding BS sequence are utilized. Similarly, other activation domains from transactivators may be utilized such as B42 acidic blob domain, VP16 acidic activity, and p53 acidic activation domain. J Estojak, R. Brent, E. A. Golemis Molecular and Cellular Biology 15:5820-5829 (1995); and H. Lee, K Hun Mok et al. JBC 275: 29426-29423 (2000). In one preferred embodiment, the IPR has five copies of the Ga14 cognate DNA binding sequence located in amino acids 1 to 148. It is contemplated that multiple copies of other binding domain recognition sequences may be utilized. For example, the binding domain sequences (BD) for LexA. The binding sites are usually located 10 to 500 bp upstream of the TATA box.

In a preferred embodiment, the BS and promoter sequence constitute an Inducible Promoter Region ("IPR") that is essentially a bipartite construct with a first component being the minimal promoter TATA box, which functions minimally alone and upstream from the minimal promoter, and a second component being at least one BS that significantly increases transcription from the bipartite promoter in the presence of an intact TA agent bound to the BS. In a preferred embodiment, the IPR has a minimal adenovirus promoter region (E. D. Lewis, J. L. Manley, Mol Cell Biol 5: 2433-2442 (1985). Utilizing several copies of the BS recognized by the BD of the TA agent allows for stronger binding of the TA agent to the RC. The number of BS to be provided ranges from 1 to about 8, preferably about 5. In accordance to the above, preferred BD element, the corresponding BS is the DNA sequence recognized by the BD. K. H. Young, Biol. Reprod. 58: 302-311 (1998). In this configuration the minimal TATA box promoter region will be able to promote only very minimal transcription in the absence of binding to the BD region by an additional transcriptional activator, in this case provided by the BD-AD chimeric protein.

In some instances the first element of the bipartite transcriptional control region consisting of the minimal promoters such as the TATA box may lead to an undesirably high level of transcriptional activity in the absence of binding of the transcriptional activator containing the BD-AD to the BS sequence. To allow a greater level of control through suppressing transcription from the minimal promoter TATA box in the absence of binding to the BS by a transcriptional activator, an additional tetracycline regulated repressor or preferably a tetracycline regulated suppressor element is placed downstream of the minimal promoter as shown in FIG. 5. This DNA sequence element termed a TetO will bind a tetracycline repressor protein or a tetracycline suppressor protein in the absence of tetracycline as shown in FIG. 5. In the presence of tetracycline the tetracycline responsive repressor or suppressor protein will be released from the TetO element and relieve the repression of transcription from the bipartite transcriptional control region containing the BS and minimal TATA region. It is contemplated that other control elements may be used.

In one exemplary embodiment, a transcriptional control region is located downstream of the BS and the promoter region (which promoter region may comprise a TATA box). In accordance to a preferred embodiment, the element downstream of the promoter region on the Reporter Construct is at least one copy of a 21-nucleotide TetO promoter region. N. F. J. van Poppel, J. Welagen, et al. International Journal for Parasitology 36: 443-452 (2006). Preferably, the RC comprises at least one to about six TetO promoter repeats, more preferably about four TetO promoter repeats. When the RC is located in a TetS cell which comprises a tTS gene product, transcription over the TetO promoter region is blocked. A preferred such TetS/tTS cell line is a HeLa cell line derivative, for example the cell line from Clontech: HEK 293 tTS, Catalog #631146; or HeLa 293 tTS, Catalog #631147. Upon addition of tetracycline, the TetO promoter is not bound by tTS. In one preferred embodiment of the invention, the Reporter Construct includes additional components to enhance the efficiency of the method of evaluating protease activity. One such component consists of a transcription silencing or inhibition sequence that is used to prevent transcription of the reporter product unless the appropriate conditions are present. For example, as shown in FIG. 5, several copies of the Tet operons (TetO) may be placed down-stream from the promoter. N. F. J. van Poppel, J. Welagen, et al. International Journal for Parasitology. 36:443-452 (2006). If the RC is introduced into cell lines that express transcription silencer tTS the transcription of the reporter will be repressed. Addition of tetracycline will remove the tTS from binding to the TetO and the promoter will be highly activated. A person of ordinary skill in the art would recognize that other similar transcription inhibitors may be utilized. It is understood that an increase in the number of copies of the TetO is directly related to the level of transcription of the reporter, as more copies of the inhibitor bind to the region tighter.

The AD element of the TA agent (in accordance to the preferred embodiment described above, the AD is NFκB) is then free to facilitate transcription. This additional control level allows for a tightly controlled system. For example, absent tetracycline, there is no reporter gene product and the expression is not particularly "leaky." Background transcriptional levels in the absence of expression the TA or release of the BD-NFκB chimera can be measured.

The IPR comprising the above elements is upstream and controls transcription of one or more reporter genes. In a preferred embodiment of the present invention more than one reporter may be utilized to evaluate protease activity. For example, two different fluorescent molecule sequences may be included. Other reporter couples may also be utilized, such as a fluorescent reporter and an antibiotic resistance sequence. The two sequences may be translated as separate molecules or might produce a chimeric product. In one preferred embodiment, the two reporters are part of a single translation product. In a yet more preferred embodiment, the two reporter molecules are separated by a cleavable linker. In one example, as shown in FIGS. 2 and 4, a Venus gene product is fused to the Gaussia luciferase gene (GLuc) gene product and the two reporter proteins are linked by a "self-cleavage" peptide 2A sequence of the foot-and-mouth disease virus (FMDV). M. D. Ryan and J. Drew, *Foot-and-mouth disease virus 2A oligopeptide mediated cleavage of an artificial polyprotein*, The EMBO Journal 13:928-933 (1994). A person of ordinary skill in the art would recognize that other self-cleavage peptides may be utilized to link the two reporters or that the two reporters may be active as part of a fused protein product, not necessitating separation into two protein products. The 2A cleavage site allows the production of secreted GLuc activity into the medium and cell fluorescence from Venus expression. Inclusion of both reporter genes permits instantaneous examination of cells microscopically for Venus YFP production as well as detection of bioluminescence in plate readers. Because the GLuc product is released into the media in which the cells are grown, over-expression of the GLuc reporter can be easily measured by methods recognized by a person of ordinary skill in the art. An alternative method to express two proteins from one transcript (one RNA expressed from one promoter) is to insert the Internal Ribosome Entrance Site (IRES) in between two genes. Yury A. Bochkov and Ann C. Palmenberg BioTechniques 41:283-292 (2006).

The system may be utilized to evaluate the activity of the protease that specifically recognizes the PS of the TA agent, in vivo. For example, when the construct is expressed in cells that contain a RC, the level of expression of the reporter product indicates the presence of the chimeric BD-AD product, which is a function of the activity of the protease in the same cell.

When the protease substrate contains trans-membrane components, the effect of the BD-AD components are disabled. For example, the botulinum neurotoxin protease substrates in their natural form contain palmitoylated residues that localize the proteins to vesicular membranes. Lane, S. R. and Y. C. Liu. Journal of Neurochemistry 69: 1864-1869 (1997). As a result, the PS utilized in the BD-PS-AD constructs described above exclude the palmitoylated residues of the substrate. Localization to the cell membrane can be avoided simply by deleting palmitoylated residues from the construct. A person of ordinary skill in the art would recognize that in some embodiments, instead of excluding the palmitoylated residues from the construct, the construct may be engineered to prevent palmitoylation of those residues and inhibit localization of the construct to vesicular membranes.

Palmitoylation and the resulting localization to the cell membrane, however, can also be used in an alternative preferred embodiment of the present invention. In such embodiment, a palmitoylated protease substrate is attached to the transcription enhancer domain as shown in FIGS. 3 and 4. This configuration is described below as the BD-AD-PS or as AD-BD-PS where the order of BD-AD and AD-BD are interchangeable. Alternatively, the protease substrate may be attached to the transcription enhancer element resulting in a PS-BD-AD configuration. In examples of these preferred embodiments, the botulinum neurotoxin substrate is provided as shown on FIG. 4*a* (BD-NFκB-VAMP) and FIG. 4*b* (SNAP-25-BD-NFκB), where the BD in this preferred embodiment is the Gal4 binding domain. In another preferred embodiment, the full length syntaxin1a with the BD-AD domains fused to syntaxin1a N-terminus. The C-terminal transmembrane domain of syntaxin1a anchors the BD-AD-syntaxin1a full length molecule to the membrane of the presynaptic terminal.

Due to the potential limitations of the Cleavage-on BoNT/A cleavage assay, one potential solution which represents a separate embodiment of this invention, the BD-AD domain may be fused to the protease substrate PS in this case SNAP25 amino acids 104 to 206 (lacking the palmitoylated cysteine residues present in SNAP25, amino acids 95 to 103) which is further fused to either syntaxin1a full length molecule to anchor the entire fusion molecule BD-AD-SNAP25 (104 to 206)-syntaxin1a full length (1-288). This arrangement will not only address potential limitations of the SNAP25 full length (1-206)-BD-AD Cleavage-on system for BoNT/A but the BD-AD-SNAP25 (104 to 206)-syntaxin1a full length (1-288) will also function as a Cleavage-on indicator for BoNT/C1 due to cleavage of both the SNAP-25 and the syntaxin1a molecules and for BoNT/E in SNAP25. There are potential advantages to using syntaxin1a to anchor the BD-AD-SNAP25 molecule to the presynaptic membrane. The principle advantage is that the syntaxin1a targeting and localization to the presynaptic membrane essentially identical to that of SNAP25 provide correct localization of the SNAP25 substrate. Additionally the BoNT/A LC is trafficked to the presynaptic membrane similar to the syntaxin1a trafficking allowing localization of protease substrate and BD-AD-SNAP25 (104 to 206)-syntaxin1a full length (1-328). In another embodiment of the present invention, the TA agent is a BD-AD-SNAP25 (104-206)-VAMP-2 construct. The BD-AD-SNAP25 (104-206)-VAMP-2 construct is a universal botulinum protease system that can be utilized as an assay for essentially all BoNT serotypes (BoNT/A, C1, and E cleave SNAP-25 and BoNT/B, D, F, and G cleave VAMP-2).

The reporter sequence of the RC may correspond to the sequence a fluorescent protein, a bioluminescent protein or any other protein that allows for the quantification of a signal upon expression of the gene. It is contemplated that yellow fluorescent protein (YFP), green fluorescent protein (GFP), cyan fluorescent protein (CFP); blue fluorescent protein (BFP), red fluorescent protein (RFP) and fluorescing mutants thereof, may also be utilized. Bioluminescent proteins such as Gaussia luciferase, renilla luciferase, click beetle, and firefly luciferase may also be used to quantify the activity of the reporter vector. In one preferred embodiment, the reporter sequence may consist of the Venus yellow fluorescent protein. Nagai T., Ibata K., Park E. S., et al. Nature Biotechnol 20: 87-90 (2002).

The system may be utilized to create a genetically engineered cell line containing one or more of the constructs described above. The constructs may be incorporated into one or more vectors for expression in a particular type of cell. The constructs may be stably integrated in the cell, or may reside on transformation vectors. The methods and vectors are well known in the art. The methodologies used for transfection and transduction into cells are well known in the art. Laura Bonetta, *The Inside Scoop—Evaluating Gene Delivery Methods*, Nature Methods 2: 875-883 (2005). In a preferred embodiment, one or more of the constructs are integrated via lentiviral vectors. In a further preferred embodiment, the lentiviral vectors are self-inactivated ("SIN") lentiviral vectors. A person of ordinary skill in the art would recognize that the vector may include other selection markers such as antibiotic resistance markers in order to distinguish cells that contain the constructs from those that do not.

Another preferred embodiment of the present invention provides a method for creating a genetically engineered cell line. In a first step of the method, eukaryotic cells, such as 293-tTS cells, are transduced with a vector containing the RC comprising a regulated reporter gene, expressed from a minimal promoter controlled by five copies of the Gal4 BS. IN other preferred embodiments, four copies of the synthetic tetracycline operator are also included ("the G5T04 promoter") as described above.

The system is used to evaluate the activity of specific proteases, such as botulinum neurotoxins. In the first step, a lentivirus vector containing the RC with the Gal5/TO4 promoter and the Venus and GLuc genes is transfected into mammalian 293-Ts cells. The cells are then transfected with a lentivirus vector containing either the BD-SNAP-25-AD construct or the BD-VAMP-2-AD construct. The construct is stably integrated. The cell line is engineered to further comprise a gene construct encoding BoNT/LC-B to generate the final reporter cell line for evaluating the activity of the various botulinum neurotoxin proteases. In these final cell strains, expression of BoNT/LC cleaves the SNAP-25 or VAMP-based transactivator fusion protein, separating the DNA binding domain from the activator domain and, consequently, cells fail to express the Venus and luciferase reporter genes. Alternatively, the protease is transduced into the cell. The same method may be utilized for identifying the activity of other protease-substrate or binding domain-binding site couples, as described above.

The reporter cell lines containing the RC, TA agent, and PC, are utilized to identify protease inhibitors. In one preferred embodiment, the cell lines are utilized for high throughput screening of protease inhibitors, such as botulinum neurotoxin inhibitors. When intact, the chimeric transcription factor activates the G5 or G5TO4 promoter resulting in expression of the Venus and GLuc reporter genes, and when cleaved by the botulinum neurotoxin light chain, the expression of the reporter genes is turned off. As described previously, this system is referred to as a "cleave-off" system and is ideal for small molecule BoNT/LC inhibitor screening because inhibition of BoNT will result in an increase in reporter signal ("gain-of-signal" assay), reducing the frequency at which false positives are detected. In the presence of BoNT/LC inhibitors, the transcription factor will no longer be cleaved, resulting in restoration of the expression of the Venus and GLuc indicators.

The cell lines are used in a high throughput screening assay, where the system is exposed to potential inhibitors. In one embodiment of the present invention, the systems may be utilized to identify inhibitors present in available chemical libraries or by testing specific molecules of interest. One such method utilizing libraries is discussed in Examples 4 through 6.

One embodiment of the present invention presents a cellular, gain-of-signal, bioluminescent, reporter screen. In a preferred embodiment, the present invention identifies endopeptidase inhibitors of neurotoxins, such as BoNT/A LC and BoNT/B LC, through cell-based reporter HTS. These endopeptidase inhibitors are small molecules, which inhibit neurotoxins, such as BoNT/A or BoNT/B. The engineered cell lines used in accordance to one preferred embodiment exhibit a low basal reporter signal, but produce a much higher amplified light signal (>10×) when small molecules inhibit the peptidase activity of the BoNT/LCs. This approach provides a means to identify inhibitors that are active in cells against BoNT/LC interacting with SNAP-25, VAMP-2, syntaxin1a, and other neurotoxins. Each cell-based BoNT/LC or HTS screening assay provides a convenient counter screen for the other assay. Likewise, employing serially a cleave on and a cleave off assays may serve as counter screening assays. The purpose of these counter screen assays is to determine, for example, the mechanism of action in accordance to the invention as opposed to other, general toxicity phenomena. Such testing of the system includes cytotoxicity assays or determination of cleaved transcriptional activator molecules, and quickly remove false positives and rapidly identify the most selective and non-toxic neurotoxin inhibitors. One manner of screening false positives includes the analysis of the transcriptional activator molecule in a system that seems to have affected the expression of the reporter molecule. The screens for the false positives (e.g. inhibitors that worked by some mechanism unrelated to release or break down of the TA molecule) relay on, for example, the analysis of the size of the TA molecule by a separation column and antibodies recognizing the TA molecule. Therefore, one embodiment of the invention provides methods for the identification of "drug-like" small molecules, which inhibit neurotoxin cleavage of its substrates, such as SNAP-25, VAMP-2, syntaxin1a, in neurons through cell based HTS.

The cell-based screening approach described here provides significant benefits over any in vitro enzymatic screens, since compounds must reach the intracellular milieu and inhibit neurotoxins, such as BoNT/A or BoNT/B, in the cytosol from cleaving their substrates, such as SNAP-25, VAMP-2, syntaxin1a. Therefore, both the toxin and its substrate are in a clinical, in vivo milieu. The toxin function is very likely different within the cell as opposed to cell free enzymatic activity. The use of large substrate fragments of 70-100 amino acid residues is one of the key advantages to these cell based assays. Since the active site may encompass proteins larger than the exosites, it allows the detection of cleavage at sites not normally considered an exosite.

The method and system disclosed herein may be used to identify and prioritize inhibitors of various neurotoxins, such as botulinum neurotoxins A and B for optimization into therapeutics. The method may be further used to construct, validate, and apply mammalian cell-based primary reporter screens for inhibitors of neurotoxins, such as BoNT/A and BoNT/B, to libraries of diverse compounds. Hits may be confirmed by re-assay in triplicate, and false positives may be eliminated by using multiple BoNT-based assays or non-toxin assays as counter-screens for each other and the other methods as described above. The method disclosed in this application further provides for a cellular, gain-of-signal, reporter screen. These screens may be applied libraries of compounds and follow-up with biochemical assays as a secondary validation to identify potential inhibitors. The validated hits may be characterized thoroughly to ensure that they act specifically on the botulinum neurotoxins both in vitro and in neuronal cell model systems and that they exhibit minimal cytotoxicity.

In one embodiment the systems and methods described herein provides for the identification and development of highly potent small molecule inhibitors for the treatment of BoNT induced poisoning. Small molecule BoNT LC inhibitors can penetrate neurons and provide protection both pre- and post-toxin exposure. In other embodiments the systems and methods described here may be used for identification of small molecule inhibitors to other protease substrate pairs that may be important in causing pathogenic states. Such protease substrate pairs may include anthrax lethal factor, caspases, ubiquitin proteases, sumo proteases, ubiquitin-like molecule processing protease, autophagy related processing proteases such as ATG4, viral encoded proteases such as alpha virus NSP2 and HIV proteases.

The BoNTs are but one example of the many ways in which a system to identify protease inhibitors may be utilized. A person of ordinary skill in the art would recognize that the constructs and methods described herein may be utilized for the evaluation of other proteases, their activity and their inhibitors. While the range of possibilities may include nearly any substrate and protease combination some specific example would include anthrax lethal factor zinc metalloprotease (LF) and its cognate substrate MAPKK, viral processing proteases such as the NSP2 protease of alpha viruses and its cognate substrate NSP1-4, ubiquitin and ubiquitin like molecule processing proteases, caspases, ubiquitin proteases, sumo proteases, ubiquitin-like molecule processing protease, autophagy related processing proteases such as ATG4, viral encoded proteases such as alpha virus NSP2 and HIV proteases. For the screening of small molecule inhibitors, cell based systems that have a suppressed signal when the protease is active in cells but generate an increase in signal when the protease is inhibited by small molecules in cells is preferable for the rapid high-throughput screen of small molecule inhibitors. This preference is due to the fact that an increase in signal in the presence of a "positive hit" or the presence of an active protease inhibitor compound is more effective in high throughput screening (HTS) generally.

Means for detecting the presence of a protease activity in cells may be important. For instance if a mass exposure to BoNT were to occur, rapid triage of those requiring immediate therapy with limited resources vs. those who may not have actually been exposed but feel ill (so called walking well) may be needed. Similarly the current "gold standard" or primary means of assaying the potency and efficacy of BoNT pharmaceutical preparations relies on the injection of toxin into mice for establishment of mouse LD50 units. This method requires extensive use of live animals in a lethal assay. It would be desirable to limit or eliminate the use of such live animal assays. A cell based assay which might reliably detect the presence and quantify the activity of the BoNT is needed. Cell based assays for detecting the presence of a protease in the cells such as the BoNT LC protease are best configured with a system that turns on an indicator signal or signals with the presences of the protease in the cell. In one embodiment of the present invention, cells expressing the TA agent and RC in the "cleave on" configuration (BD-AD-PS) are utilized to identify the presence of known proteases in a sample. In such embodiment, an environmental sample is presented to cells containing the TA and RC constructs. If target protease, e.g., BoNT/LC A, is present, it will enter the cell, cleave the TA at the PS, releasing the AD-BD fragment, which in turn enhance transcription of the reporter gene in the RC.

Example 1. Expression of pBD-NFκB in Mammalian Cells

A RC in accordance with one embodiment of the present invention, containing a synthetic promoter G5/T04 was transfected by a lentiviral vector into cells. The RC was co-transfected with a plasmid expressing a Gal4 binding domain fused to the NFκB activator fusion (pBD-NFκB) (the TA agent) into HeLa-tTS cells. The transfected cells constitutively express the tetracycline transcription silencer tTS (Clontech). The cells were grown in a 6-well plate to approximately 80% confluence. Six hours after transfection, 1 ug/ml of tetracycline was added to the media of the test cells. Tetracycline was not added to the media of cells used as a control. Culture medium was collected two days post-transfection for the Gaussia luciferase (GLuc) assay. Monique Verhaegen and Theodore K. Christopoulos Anal. Chem., 74:4378-4385 (2002). Venus expression was observed with a fluorescent microscope. The relative light units (RLU) of the cells cultured in medium containing 1 μg/ml tetracycline is 16 fold higher than that of cells cultured in the absence of tetracycline as measured by luminometer. Additionally, there is Venus expression in the cells cultured in medium containing tetracycline but no Venus expression in cells grown in medium lacking tetracycline. Thus, (1) the synthetic promoter G5TO4 is functional. It can be highly activated by a transactivator, such as BD-NFκB that binds to Gal4 binding sites. Both GLuc and YFP expression are highly activated in the presence of tetracycline; (2) The GLuc gene is a very sensitive and convenient reporter. In these experiments, ninety-five percent of Gaussia luciferase is secreted into the culture medium; thus, GLuc activity can be directly measured from culture medium by a luminometer. In light of this controlled reporter gene expression, low and measurable backgrounds of reporter gene expression, and convenient use, the promoter-reporter system described in this application is useful for high throughput screening.

The novel RC was transduced into 293-tTS cells by lentiviral vector. Lentiviral vector particles carrying the RC were produced by co-transfecting 3.5 μg of the transducing plasmid with 7.1 μg HIV-1 gag-pol helper construct (Synaptic Research), and 2.8 μg VSV-G expression plasmid (Synaptic Research) onto 80-90% confluent 293FT cells (Invitrogen) cultured in 100 mm plates. Culture medium that contained the budded viral vectors was collected 48 hours after transfection and was cleared of cell debris by centrifugation at 2,000 RPM for 10 minutes at 4° C. (Sorvall RT 600D). The cleared viral supernatant was further concentrated by ultracentrifugation at 25,000 RPM for 90 minutes at 4° C. (Beckman Coulter Optima™ XL-100K). Lastly, the viral vector pellet was soaked in 50 μl (1/200 the original volume) of culture medium overnight, resuspended, and stored at −85° C. until needed for transduction. The resulting viral vector particles were used to transduce 293T-tTS cells (Clontech®) that constitutively express the tetracycline transcription silencer tTS. Single cell colonies were cloned by cloning rings and tested for functionality by transient transfection of the expanded cells with a pBD-NFκB construct, which expresses the chimeric transactivator BD-NFκB. The transfected cells were cultured in the presence and absence of 1 μg/ml tetracycline. Two days after tetracycline induction, YFP fluorescence (Venus gene expression) was observed with a fluorescent microscope and Gaussia luciferase gene expression was measured by a luminometer.

We analyzed 25 clones, and results of six clones are shown in FIG. 6. We selected clone #17, which exhibits very low basal activity and can be activated more than 14 fold by the addition of tetracycline. Accordingly, the reporter molecules were induced by the activator agent and the system has the necessary attributes for high throughput screening

Example 2. tTS Cells Comprising the RC and TA Agent

A gene for the regulatory component, a transactivator chimeric fusion protein consisting of the appropriate BoNT substrate, SNAP-25 for BoNT/A and VAMP-2 for BoNT/B, sandwiched between a Gal4 DNA binding domain (amino acids 1-148) (Gal4/BD or BD) and the NFκB transactivation domain (NFκB/AD or AD) was transduced into the cells that have the novel Reporter construct as described in Example 1.

Example 2A

The BD-PS-AD constructs, in which the protein substrate does not contain palmitoylated residues, were constructed synthetically and introduced in cells containing the RC. The TA agent encoding either 103 amino acid residues around the cleavage site of SNAP-25 (residues 104-206) or 70 amino acid residues around the cleavage site of VAMP-2 (residues 25-94) fused between the Gal4 DNA binding domain and the NFκB transactivator domain were used. The reporter cell line clone #17 from Example 1 was further transduced with a lentiviral vector that carries the BD-VAMP-NFκB transactivator gene construct. Six single cell clones were selected and analyzed for the ratio of bioluminescence in the presence and absence of tetracycline. See FIG. 7. The transduced cells were subjected to appropriate selection (G418, blasticidin, and puromycin), and single-cell clones carrying stable integrations of both the reporter and the VAMP-2 transactivator fusion were obtained. The reporter gene in clone #32 was routinely/repeatedly activated more than 200-fold when 1 μg/ml tetracycline was added to the culture medium.

A similar process is used to create a cell lines containing other chimeric transactivator constructs. For example, the cell lines containing the reporter vector are further transfected with a BD-SNAP25-NFκB or a BD-syntaxin1a-NFκB gene construct. Alternatively, more than one transcriptional activator construct, each containing another BoNT substrate, is created. In addition, the binding domain (BD) and the transactivation domain (NFκB) may be replaced with any DNA binding domain and transactivation domain as long as the binding sites of the Reporter construct are changed correspondingly. Single cell clones carrying the RC and TA agent are selected and their functionality are evaluated as described for clone #32.

The functionality of clone #32 was analyzed in a 96-well microplate in order to demonstrate that signal strength and the signal:background ratio are adequate for use in high throughput screening. Duplicates of three groups of 3 wells each were seeded with a low (group 1), medium (group 2), and high (group 3) density of cells. One day after culturing cells in the presence or absence of 1 μg/ml tetracycline, 5 μl of 5-fold diluted culture medium was transferred to a second microplate and luminescence was measured in a plate reader. The luciferase activity in the medium of cells treated with tetracycline was 200-fold higher than that observed from culture medium of cells not treated with tetracycline. See FIG. 8. That result was consistent for each member of each of the three groups. In addition, the basal activity in cells non-treated with tetracycline was extremely low. Luminescence was measured. The luminescence was increased 200 fold by transactivation in the presence of tetracycline and the intact DB-PS-TA construct. See FIG. 8.

Example 2B

The "cleave-on" method was evaluated by the transcriptional activator constructs encoding either 103 amino acid residues around the cleavage site of SNAP-25 (residues 104-206) or 70 amino acid residues around the cleavage site of VAMP-2 (residues 25-94) fused upstream or downstream of the chimeric transactivator BD-NFκB/AD, respectively, as shown in FIGS. 3 and 4. As a result of the palmitoylated residues of the botulinum substrates, the SNAP-25 and VAMP-2 segments are expressed on the cellular presynaptic plasma membrane tethering BD-NFκB/AD to the membrane. FIG. 9 shows examples of the results of experiments conducted using both configurations.

Example 3. Further Validation of Constructs in Stable Cell Lines

Validation of the cleave off system utilizing the VAMP2-based TA construct and BoNT/LC-B as the PC, and the TetO containing RC was accomplished in stable cell lines. Clone #32, which carries stable integrations of both the reporter and the VAMP2 transactivator, was used to construct the final inducible indicator cell line by lentiviral transduction of the BoNT/LC-B PC. With all three components of the indicator system (RC, TA, and PC) stably incorporated into this complete cell line (Clone #12), the system was tested by evaluating the decrease in GLuc expression over the course of 48 hours immediately following induction with tetracycline. GLuc assays were performed before replacing the media with fresh culture media every 24 h. GLuc activity expressed in terms of RLU was measured using a luminometer and showed an approximate 15-fold reduction in GLuc signal after 48 hours induction of the BoNT/B LC from the Tet-regulated PC FIG. 10. This result demonstrates that the fully assembled system with the RC, cleave-off TA, and the PC is suitable for high-throughput screening of BoNT/B LC inhibitors. The system in this configuration will exhibit an increase in signal with inhibition of the LC protease.

Validation of the cleave-on system utilizing the VAMP2-based TA construct and BoNT/LC-B as the PC, and the TetO containing RC was also accomplished in stable cell lines using the same procedure described above. The results show a nearly 40-fold increase in GLuc signal after 48 hours. FIG. 10. The system in this configuration will exhibit a decrease in signal with inhibition of the LC protease, but if more appropriate for detecting the presence of BoNT/LC-B protease.

Example 4. Cleave Off System Reduces Gene Expression

To demonstrate their functionality, the SNAP-25 and VAMP-2 chimeric transcriptional activators were cloned into self-inactivated (SIN) lentiviral vectors and co-transfected into 293T-tTS cells with the reporter construct together with various BoNT/LC gene constructs (wild-type LC-A, an inactive mutant LC-A, and wild-type LC-B). The cells were treated with 1 μg/ml tetracycline. Gaussia luciferase (GLuc) activity was measured with a luminometer and Venus YFP expression was observed by fluorescent microscopy. The results are shown in FIG. 9. The results confirmed that the reporter is turned off by cleavage of the transactivator. The chimeric BD-SNAP25-NFκB transactivator strongly activates the G5TO4 promoter when co-transfected with inactive mutant BoNT/A-LC mLC-A and Gal4/BD-SNAP25-NFκB/AD, which was used to mimic the presence of a potent BoNT/LC-A inhibitor, but not when co-transfected with the wild-type BoNT/A-LC LC-A and Gal4/BD-SNAP25-NFκB./AD. The chimeric Gal4/BD-VAMP-NFκB transactivator/AD transactivates the G5TO4 promoter when transfected with the BoNT/A-LC expressing plasmid because it is not cleaved by BoNT/A-LC. The chimeric transcription activator construct Gal4/BD-VAMP-NFκB/AD does not activate the reporter when co-transfected with wild-type BoNT/LC-B LC-B and Gal4/BD- VAMP-NFκB/AD because the transcription factor is cleaved. The Gaussia luciferase activities expressed as RLU values are consistent with the visualized YFP fluorescence and provide quantitative measurements of the reporter response—20-fold and 23-fold in the SNAP-25 and VAMP transactivator systems, respectively, for uncleaved vs. cleaved transactivators.

Two BoNT constructs consist of the streptavidin binding protein (SBP), the cyan fluorescent protein (CFP), and BoNT/A-LC or BoNT/B-LC fused sequentially and in frame. These two constructs, SBP-CFP-BoNT/A-LC and SBP-CFP-BoNT/B-LC, have been cloned into the lentiviral vector pLenti4/TO/V5-DEST (Invitrogen, Inc., Catalog No. K4965-00). The fusion genes are expressed from a modified CMV promoter that has two copies of Tet operator inserted immediately upstream of the TATA box. Binding of the Tet responsive repressor (TRex, Invitrogen) or transcription silencer tTS (Clontech) silences the promoter. However, in the presence of tetracycline the TRex or tTS fails to bind the Tet operator, and the CMV promoter is fully active. The constructs were transfected into 293-tTS cells seeded in a 6-well plate. Expression of the BoNT/LC was detected by observing CFP expression by fluorescence microscopy. These lentiviral constructs of BoNT/A-LC and BoNT/B-LC may be used to complete the construction of the reporter cell lines.

Example 5. Complementing Stable Reporter Cell Lines with TA and PC

A) VAMP Cleave-Off

In order to evaluate the biological functionality of the reporter construction (RC) without TetO, this RC was stably integrated into HEK 293 cells with lentiviral vectors as described previously. Using this stable reporter cell line as a platform, the VAMP cleave-off system was tested by complementation with the corresponding PC (BoNT/LC-B) and TA (BD-VAMP2-AD) plasmids using transient transfection. Immediately following transfection, the time-course expression of both Venus (YFP) and GLuc from the reporter construct was assayed. Specifically, the reporter cells were grown in 6-well sterile polylysine coated plates to approximately 70% confluence in 2 ml of complete growth medium. For transfection with transcriptional activator BD-VAMP2 (25-94)-NFκB plasmid alone, 4 μg of plasmid DNA was transfected using CalPhos Kit (Clontech Laboratories Inc.). For cells, co-transfected with BD-VAMP2-AD and BoNT/LC-B, a 1:3 ratio of TA:PC plasmid DNA was used. Plates were incubated at 37° C. overnight in $CO_2$ incubator. After 12 h, media was replaced with 2 ml fresh complete growth media and 5 ug/ml of tetracycline is added to the media to initiate the expression of BoNT-LC-B. Cells transfected only with BoNT/LC-B were used as positive control for LC-B expression. Tetracycline was not added to the media of cells transfected with only BD-VAMP2-AD, used as a control. An aliquot of the culture medium was collected at 24 h, 48 h and 72 h for Gaussia luciferase (GLuc) assays before replacing the media with fresh culture media every 24 h. GLuc activity expressed in terms of RLU was measured using a luminometer and Venus YFP fluorescence was monitored by a fluorescent microscope. Cells scraped from the plate surface from different wells at 24 h, 48 h, 72 h time intervals were washed twice with PBS and centrifuged at 10,000 rpm for 10 min at 4° C. then lysed with a gel loading Samples were run on SDS-PAGE gels and then transferred to PVDF membranes for Western blot analysis with rabbit anti-GFP (Santa Cruz Biotechnology) as primary and AP-conjugated anti-rabbit IgG as secondary antibody. FIG. 11. The success of the cell system with RC lacking the TetO, cleave-off VAMP TA, and BoNT/B LC PC, to demonstrate a decrease in signal with the cleavage of the VAMP TA by the BoNT/B LC demonstrates that this system is also appropriate for high-throughput screening of BoNT/B LC inhibitors.

B) SNAP25 Cleave-Off

Using the same stable reporter cell line described previously, the SNAP25 cleave-off system was tested by complementation with the corresponding PC and/or TA plasmids using transient transfection. Again, immediately following transfection, the time-course expression of both Venus (YFP) and GLuc from the reporter construct was assayed. Specifically, reporter cells are grown in 6-well sterile polylysine coated plates to approximately 70% confluence in 2 ml of complete growth medium without antibiotics and with serum. For transfection with transcriptional activator BD-SNAP25(104-206)-NFκB plasmid alone, 4 μg of plasmid DNA was transfected using Lipofectamine™ 2000 (Invitrogen). For cells co-transfected with BD-SNAP25-NFκB and BoNT/LcA, 4 μg of each plasmid DNA is used per well. Six hours after transfection, 5 ug/ml of tetracycline was added to the media to initiate the expression of BoNT-LC-A. Cells transfected only with BoNT/LC-A were used as positive control for LC-A expression. Tetracycline was not added to the media of cells transfected with only BD-SNAP25-NFκB, used as a control. An aliquot of the culture medium was collected at 24 h, 48 h and 72 h for Gaussia luciferase (GLuc) assays before replacing the media with fresh culture media every 24 h. GLuc activity expressed in terms of RLU was measured using a luminometer and Venus fluorescence was be monitored by a fluorescent microscope. Cells scraped from the plate surface from different wells at 24 h, 48 h, 72 h time intervals were washed twice with PBS and centrifuged at 10,000 rpm for 10 min at 4° C. then lysed with a gel loading buffer. Samples were run on SDS-PAGE gels and then transferred to PVDF membranes for Western blot analysis with rabbit anti-GFP (Santa Cruz Biotechnology) as primary and AP-conjugated anti-rabbit IgG as secondary antibody. FIG. 11.

C) SNAP25 Cleave-Off—Stable Cell Line with RC (Tetracycline Regulated)

A similar experimental procedure was followed to validate the stable reporter cell line that is regulated by TetO (Clone #17). In this case, Clone #17 was transduced by lentivirus with the BD-SNAP25-AD, which was subsequently complemented with BoNT/LC-A tet-inducible PC by transient transfection. Upon exposure to tetracycline, the GLuc signal decreased dramatically during the first 48 hours. This large decrease in signal with induction of the BoNT/LC-A LC shows the system will work for the drug screening approach and assaying decay of BoNT/LC-A.

Example 6. Expression With or Without Tetracycline

In transient transfection and stable transduction of the RC without TetO, SNAP25 (1-206)-BD-AD as the TA, and BoNT/E LC as the PC, the luciferase signal increases at least 2 fold after cleavage of the SNAP25 (1-206)-BD-AD by the BoNT/E LC despite a high basal signal level as shown in FIG. 13. The carboxyl terminal SNAP25 cleavage product after BoNT/E LC cleavage is stable. Thus there is not degradation of the BD-AD after cleavage like there is with the BoNT/A cleavage. Due to high base line signal with the SNAP25 (1-206)-BD-AD and rapid degradation of the C-terminal SNAP25 (1-206)-BD-AD, a different SNAP23 cleave-on system is used. This system consists of BD-AD-SNAP25(104-206)-VAMP full length or BD-AD-SNAP25 (104-206)-syntaxin1a full length.

Example 7. An Alternative Indicator System to Perform SNAP25 Cleave-On Assays

Any TA construct comprised of the truncated form of SNAP25(104-206) lacks palmytolation and, as a result, is not inherently capable of membrane localization. The fusion of this TA to a membrane anchor, such as VAMP2 or syntaxin1a, allows for an alternative method to perform cleave-on studies. Possible TA configurations are BD-AD-SNAP25(104-206)-VAMP2 or BD-AD-SNAP25(104-206)-syntaxin1a.

These fusion constructs are tested in the same manner as before: by transient transfection of the stable reporter cell line (lacking TetO) with both the fusion TA and either BoNT/LC-A or -B. As with all cleave-on systems, the reporter signal is low at baseline in the absence of tetracycline, but will increase upon proteolytic cleavage of the TA. After adding tetracycline, an aliquot of the culture medium is collected after 24 h, 48 h and 72 h for Gaussia luciferase (GLuc) assays before replacing the media with fresh culture media. GLuc activity expressed in terms of RLU was measured using a luminometer and Venus fluorescence was be monitored by a fluorescent microscope. The major advantage of these fused TA constructs is the ability for them to acts as universal detectors of numerous BoNT/LC serotypes. Thus, the potential for a single indicator cell line to detect the presence of any LC is realized. If the system is created in a cell line that has receptors for the BoNT toxins and can internalize the toxins efficiently, this cell line can function as a high affinity sensitive cell based biodetector for the presence of fully active BoNT. If a suitable cell line can not be found that has adequate ability to take up toxins from the environment to sensitively detect the toxins, then the affinity and sensitivity of the cell line to toxin can be increased by making a stable cell line overexpressing the necessary protein receptor and ganglioside component of the BoNT toxin cellular receptor.

Example 8. Indicator System to Detect Inhibitors of Anthrax Protease

In one example, a TA is constructed such that the PS is the full-length mitogen-activate protein kinase kinase (MEK1) (NCBI Reference Sequence: NP 002746) in the form BS-MEK1-AD. A. P. Chopra, S. A. Boone, et al. JBC 278:9402-9406 (2003). This TA construct is similarly transferred to the stable reporter cell line lacking TetO—used in a Stable Cell Line with RC (Not Tetracycline Regulated) example—by transient transfection. Accordingly, the Tet-inducible PC in this case is anthrax lethal factor (LF) protease (NCBI Reference Sequence: AAY15237), which cleaves MEK1. With all constructs present in the reporter cell, inhibitors of anthrax LF protease are screened and success candidates are chosen based on an increase in reporter signals from Venus and GLuc.

Example 9. Indicator System to Detect Inhibitors of Ubiquitin-Related Proteases

In another example, a TA is constructed such that the PS is the human small ubiquitin-related modifier1 (SUMO1) protein with the carboxyl terminal 5-AA (NCBI Reference Sequence: ABM87155). The 5-AA C-terminal peptide is cleaved by the (ubiquitin-like)-specific protease (ULP1), thus a PC construct is constructed with ULP1 as the protease (NCBI Reference Sequence: AAG33252). Both the PC and TA construct are similarly transferred to the stable reporter cell line lacking TetO by transient transfection. When the all three components, RC, TA cleave-off Sumo construct, and the ULP1 PC are expressed, the luciferase signal is diminished. This system is appropriate for high-throughput screening of SUMO protease inhibitors.

Example 10. Screening Protease Inhibitors

The final reporter cell lines is functionally validated by small molecule inhibitors of siRNA knock-down. For the BoNT/A-LC screening assay, established inhibitors (e.g., either hydroxamate compounds) are used. Since there is no small molecule inhibitors known for BoNT/B-LC, siRNAs are used that target BoNT/B-LC from Dahrmacon/Thermo-Fisher. In one embodiment of the present invention, three siRNAs per target may be developed. In addition, a scrambled siRNA is used as a control, which ensures that the knock-down is real and specific and there in no off-target effect. 293T cells are co-transfected with the siRNA and the BoNT/A-LC or BoNT/B-LC plasmids and Western blot analysis are used to choose the most effective siRNA for validating the final reporter cell lines. Then both the effective and the scrambled siRNA are used to transfect the final reporter cells. Transfection 1 μg/ml of tetracycline is added to the culture medium to initiate expression of BoNT/LC immediately after transfection. An aliquot of the culture medium is collected at day 1 through day 4 for luciferase assays. Venus fluorescence may be monitored by a fluorescent microscope. The expression of the reporters (both luciferase and Venus fluorescence) in the final reporter cells are restored by the effective siRNA.

The reporter screens are optimized by running microplates with half positive (BoNT/A-LC inhibitor or siRNA for BoNT/B-LC) and half negative (DMSO only) controls and measuring the Z' value. Conditions used to determine the effectiveness of each reporter strain include the density of microplate (96-well or 384-well), concentration of compound to be tested, DMSO concentration tolerance, temperature, degree of confluence of reporter strain before addition of test compounds, time of incubation in microplates before reading luminescence, and quantity of medium withdrawn for luciferase assay. Conditions may be changed to achieve an optimal Z' factor >0.5 J. H. Zhang, T. D. Chung, and K. R. Oldenburg, J Biomol. Screen 4:67-73 (1999). for each screen. In one preferred embodiment of the present invention the screens are conducted in 384-well dishes. 96-well dishes may be used if necessary to maintain adequate Z' factor values.

Reporter strains are grown and seeded into 96- or 384-well opaque white screening plates using a sterile Wellmate Microplate reagent dispenser (ThermoFisher, Inc.). For inhibitor screening, compound master plates are thawed at room temperature on the day of the screen, and a predetermined quantity of compound is added by using a Sciclone ALH 3000 liquid handling robot (Caliper, Inc.) and a Twister II Microplate Handler (Caliper, Inc.). Plates are then incubated under established optimal conditions of time and temperature. Then, a predetermined quantity of the cell medium is transferred to a fresh microplate with the Sciclone robot to generate an appropriate dilution. Luciferase substrate is added by means of a Wellmate reagent dispenser, and luminescence is measured in an Envision Multilabel microplate reader (PerkinElmer).

Example 11. Optimized Screening of Inhibitors

The system used to screen inhibitors is subjected to a pilot screen to assess screening conditions. The optimized assay configuration is tested in a pilot screen of ~2,000 compounds at 2-3 different concentrations. Controls are included in each plate—8 wells for 0% inhibition (DMSO only) and 8 wells for nearly complete inhibition (BoNT/A-LC inhibitor or siRNA for BoNT/B-LC). Assay plates receive appropriate reporter cells and compounds to be tested according to the protocol described above. The data obtained from this screen is used to determine variation (% CV), the hit rate at various z-score cutoffs, and may identify any problems with the assay which require resolution before HTS begins. The data from the pilot screen is then used to determine the compound concentration for the screen (probably in the range of 25-40 μM) in order to establish a hit rate between 0.1% and 1%. The criteria for designating a compound as a hit is determined in the pilot screen; however, a z-score >3 or >5 is likely suitable. The z-score for each sample is derived by subtracting the sample RLU from the mean negative control RLU and dividing the difference by the negative control standard deviation.

Example 12. Screening for Inhibitors

The method in accordance with one embodiment of the present invention may also be utilized to screen diverse compound libraries to identify and confirm protease inhibitors with IC50's of ≤10 μM.

The high-throughput cellular BoNT/A-LC and BoNT/B-LC screens described above, is applied to libraries of discrete small molecules and natural products in order to identify compounds having potent inhibitory activity against either of these botulinum neurotoxins. Hits from the screen are confirmed by re-assay, establishing that they inhibit either BoNT/B-LC or BoNT/A-LC, but not both, and by demonstrating their potency in concentration-dependent inhibition studies (IC50).

A. Compound Libraries and Sample Handling.

The NERCE library. The compound collections of the National Screening Laboratory (NSRB) of the New England Regional Center for Excellence for Biodefense and Emerging Infectious Diseases (NERCE/BEID) at Harvard Medical is used as one example of a small molecule library to be screen in the cleave off cell based BoNT screening system. This library has been assembled by a group of NERCE's chemistry consultants who screened out compounds with undesirable properties, such as poor solubility, potential detergent-like activities, lack of stability in aqueous solutions and chemical reactivity. There are currently 165,000 compounds available including some that overlap with our in-house collection. The overlap between the two libraries is ≤10%. Therefore, the combined library resource represent 300,000 distinct compounds.

B. Application of the primary BoNT/A&B-LC screens.

Compounds in a candidate chemical library are examined in 96 or 384-well format vs. the cell-based BoNT/A-LC and BoNT/B-LC cell base HTS described above. Screening library compounds are stored in 96-well master plates at 2.5 mM in 100% DMSO at −20° C. Master plates are thawed, and an amount of compound determined in the pilot screen described above are added to the assay plates by means of a SciClone ALH 3000 liquid handling robot (Caliper, Inc.) and a Twister II Microplate Handler (Caliper, Inc.), at the same time, combining 4×96-well source plates into one 384-well assay plate. The screening plates contain positive and negative controls in the first and last columns as described for the pilot screen above.

Raw data generated by the plate reader is processed as follows: relative luminescence unit (RLU) data is captured and analyzed in a semi-automated procedure by relating the plate serial number to the database entry, associating the numerical readout to each compound entry, and calculating the % inhibition and z-score. In addition, a Z'-factor calculation is performed on each plate based on the positive and negative controls; Z' values of >0.6 are considered adequate, and data from compounds in that plate are accepted into the database. All screening data, including the % inhibition, z-score, and confirmation/validation data such as the 50% inhibitory concentration (IC50) and the counter-screen results is stored in one central database (CambridgeSoft's ChemBioOffice). A structure-activity relationship on an investigated chemical series is analyzed quickly. In addition, analog compounds are identified rapidly from commercial databases, acquired, registered into the database and submitted for biological testing.

C. Hit Confirmation and Verification.

Compounds that satisfy the criteria for designation as primary hits undergo a 3-step confirmation process previously described. First, primary hits are selected from stock plates into a confirmation stock plate and replicated to produce a set of 4 confirmation assay plates. The 4 confirmation assay plates are used in the primary screening assay to generate 4 new data points for each compound. A confirmed hit displays inhibition >50% and a z-score >3 in at least 3 of the 4 replicated assays. Second, confirmed hits are counter-screened in replicate for inhibition of the other botulinum neurotoxin. Third, confirmed hits may be examined for concentration-dependent activity in FRET assays for inhibition of BoNT/A-LC and BoNT/B-LC; an IC50 is determined to rank the potency of each.

Due to the reliability of gain-of-signal cell-based assays, few false positives are encountered in the screens if the Z' factor is >0.5 throughout the screening process. False-negatives may arise due to inhibition of both the botulinum neurotoxin and processes required for generation of bioluminescence. However, these hits would likely be promiscuous and not of sufficient quality to pursue even if they were detectable. Hits that pass the counter-screen with the alternate botulinum neurotoxin will likely not be promiscuous. To validate and prioritize the primary hits, several secondary assays are applied as described below to further qualify the hits from the screen. If the hit rate is below 0.1% using the criteria established above, the hit rate may be increased by accepting lower inhibition levels for hits as long as the Z' value for the screening plate is above ~0.6, indicating a wide separation band between the negative and positive controls, and each hit is at least 3 standard deviations below the fully active control.

In the next step of a method in accordance with one embodiment of the present invention, each identified inhibitor is validated and multiple hits are prioritized by potency and selectivity. It is contemplated that validated inhibitors of BoNT/A and BoNT/B, may have IC50s of ≤10 μM, a selectivity index CC50/IC50≥10, no significant cytotoxicity, and demonstrated activity in primary neuronal cell model.

This step in one embodiment of the present invention generates the potency and specificity information necessary to prioritize screening hits/or chemotypes discovered in the HTS assays described above. In one preferred embodiment four types of activity may be assessed: (a) in vitro potency (IC50 for inhibition of the BoNT/A and BoNT/B endopeptidase activities in vitro), (b) specificity (IC50 for potency of inhibition of other endopeptidases in vitro, BoNT/F, anthrax lethal factor (AT-LF), and a panel of human matrix metalloproteases, MMP's; and test of chelation properties), (c) cytotoxicity (i.e., CC50 of the compounds on mammalian cells in culture), and (d) in vivo potency (i.e., IC50 for inhibition of the BoNT/A SNAP-25 cleavage or BoNT/B inhibition of VAMP cleavage activity in primary rat neurons; and rescue of axonal growth inhibition). Successful compounds exhibit little or no detectable cytotoxicity or activity on other unrelated endopeptidases, but provide potent and specific rescue of BoNT/A and/or BoNT/B action in vitro and in isolated neurons.

Rat Neuronal Cell SNAP-25 Cleavage Assay. As described previously, cells are harvested from 7-8 day old rat cerebella, washed and cultured in 6-well plates, and grown over a week with media changes. Once the cells have become networked neutrally, they are preincubated with compounds or diluent (DMSO) for 15 min. Cells are then inoculated with BoNT/A and incubated for 3 hours at 37° C., 5% CO2 before harvesting. Cells are treated with 1 M NaOH to inactivate the BoNT and are scraped from the plate surface prior to centrifugation and lysis with a gel loading buffer. Samples are run on SDS-PAGE gels and then transferred to membranes for immunoblot analysis with rabbit anti-SNAP-25 and then HRP-conjugated goat anti-rabbit IgG. Band intensities are read and normalized using scanning densitometry.

The invention has been described with references to preferred embodiments. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

What is claimed is:

1. A system for assessing protease activity in a mammalian cell, the system comprising:

(a) a transcriptional activation agent comprising:

(i) a nucleic acid binding domain;

(ii) a protease substrate domain comprising SNAP-25 or a fragment thereof, and VAMP-2 or a fragment thereof, the fragments being cleavable by an exogenous protease expressed outside of the cell nucleus, the protease being botulinum neurotoxin; and (iii) a transcriptional activation domain for an inducible promoter; and (b) a reporter construct incorporated into the DNA of the cell, the reporter construct comprising:

(i) a Gal4 or LexA binding site;

(ii) an inducible promoter region; and (iii) a reporter gene;

wherein the binding site, inducible promoter, and reporter gene are all functionally connected; and wherein the reporter gene is expressed upon binding of the nucleic acid binding domain of the transcriptional activation agent to the reporter construct binding site.

2. The system of claim 1, further comprising a protease or protease candidate capable of cleaving the protease substrate domain.

3. The system of claim 2, wherein at least one of the transcriptional activation agent, protease, or protease candidate is expressed from a nucleic acid construct.

4. The system of claim 1, wherein the reporter gene encodes a fluorescent protein or a bioluminescent protein.

5. The system of claim 1, wherein the reporter gene construct comprises one to eight identical or different binding site sequence repeats.

6. The system of claim 1, wherein the reporter gene construct comprises five identical or different binding site sequence repeats.

7. The system of claim 1, wherein the inducible reporter region comprises a TATA promoter region.

8. The system of claim 1, wherein:

(i) the protease substrate domain is at a first end of the transcriptional activation agent and is bound to a membrane; and (ii) the binding domain and the transcriptional activation domain are both at a second end of the transcriptional activation agent, so that cleavage of the protease substrate domain releases the binding domain and the transcriptional activation domain from the membrane, producing a functional transcriptional activation agent fragment.

9. The system of claim 2, comprising mRNA expressed from a nucleic acid construct, wherein the mRNA expresses the transcriptional activation agent, protease, or protease candidate.

10. The system of claim 2, comprising cDNA expressed from a nucleic acid construct, wherein the cDNA expresses the transcriptional activation agent, protease, or protease candidate.

11. The system of claim 1, wherein the transcriptional activation domain is NF-κB.

* * * * *